United States Patent
Bepler et al.

(10) Patent No.: US 11,532,378 B2
(45) Date of Patent: Dec. 20, 2022

(54) PROTEIN DATABASE SEARCH USING LEARNED REPRESENTATIONS

(71) Applicant: NE47 Bio, Inc., Hillsborough, NC (US)

(72) Inventors: Tristan Bepler, Hillsborough, NC (US); Bonnie Berger Leighton, Newtonville, MA (US)

(73) Assignee: NE47 Bio, Inc., Hillsborough, NC (US)

( * ) Notice: Subject to any disclaimer, the term of this patent is extended or adjusted under 35 U.S.C. 154(b) by 0 days.

(21) Appl. No.: 17/533,567

(22) Filed: Nov. 23, 2021

(65) Prior Publication Data

US 2022/0165356 A1 May 26, 2022

Related U.S. Application Data

(60) Provisional application No. 63/117,255, filed on Nov. 23, 2020.

(51) Int. Cl.
 *G01N 33/48* (2006.01)
 *G01N 33/50* (2006.01)
 (Continued)

(52) U.S. Cl.
 CPC ......... *G16B 30/10* (2019.02); *G06F 16/2255* (2019.01); *G06F 16/24534* (2019.01);
 (Continued)

(58) Field of Classification Search
 CPC ..... G16B 30/10; G16B 40/20; G06F 16/2255; G06F 16/24534; G06N 3/0445; G06N 3/08
 See application file for complete search history.

(56) References Cited

U.S. PATENT DOCUMENTS

2021/0081728 A1\* 3/2021 Lai .................. G06V 10/255

FOREIGN PATENT DOCUMENTS

| CN | 111402953 A | 7/2020 |
| CN | 111667884 A | 9/2020 |
| CN | 111696624 A | 9/2020 |

OTHER PUBLICATIONS

Ayoub et al. RUPEE: A fast and accurate purely geometric protein structure search. PloS One, vol. 14, Mar. 15, 2019, article e0214712, 17 pages.*

(Continued)

*Primary Examiner* — Russell S Negin
(74) *Attorney, Agent, or Firm* — David H. Judson

(57) ABSTRACT

A method for efficient search of protein sequence databases for proteins that have sequence, structural, and/or functional homology with respect to information derived from a search query. The method involves transforming the protein sequences into vector representations and searching in a vector space. Given a database of protein sequences and a learned embedding model, the embedding model is applied to each amino acid sequence to transform it into a sequence of vector representations. A query sequence is also transformed into a sequence of vector representations, preferably using the same learned embedding model. Once the query has been embedded in this manner, proteins are retrieved from the database based on distance between the query embedding and the protein embeddings contained within the database. Rapid and accurate search of the vector space is carried out using exact search using metric data structures, or approximate search using locality sensitive hashing.

17 Claims, 16 Drawing Sheets

(51) Int. Cl.
    *G16B 30/10*     (2019.01)
    *G06F 16/2453*     (2019.01)
    *G16B 40/20*     (2019.01)
    *G06N 3/08*     (2006.01)
    *G06N 3/04*     (2006.01)
    *G06F 16/22*     (2019.01)

(52) U.S. Cl.
    CPC .............. *G06N 3/0445* (2013.01); *G06N 3/08* (2013.01); *G16B 40/20* (2019.02)

(56) References Cited

OTHER PUBLICATIONS

Bepler et al. Learning protein sequence embeddings using information from structure. arXiv: 1902.08661v2, Oct. 16, 2019, 17 pages.*

Mao et al. AmoebaContact and GDFold as a pipeline for rapid de novo protein structure prediction. Nature Machine Intelligence, vol. 2, Dec. 23, 2019, pp. 25-33.*

Ng et al. Finding all longest common segments in protein structures efficiently. IEEE/ACM Transactions on Computational Biology and Bioinformatics, vol. 12, pp. 644-655. (Year: 2015).*

Nigam et al. Crop yield prediction using machine learning algorithms. Fifth International Conference on Image Information Processing (ICIIP). pp. 125-130. (Year: 2019).*

Senior et al. Improved protein structure prediction using potentials from deep learning. Nature, vol. 577, Jan. 15, 2020. 22 pages.*

Shibuya S. Searching protein three-dimensional structures in faster than linear time. Journal of Computational Biology, vol. 17, pp. 593-602. (Year: 2010).*

Tai et al. Improved semantic representations from tree-structured Long Short-Term Memory networks. arXiv:1503.00075v3, 11 pages. (Year: 2015).*

PCT/US202/060533, International Search Report and Written Opinion, Mar. 22, 2022.

* cited by examiner

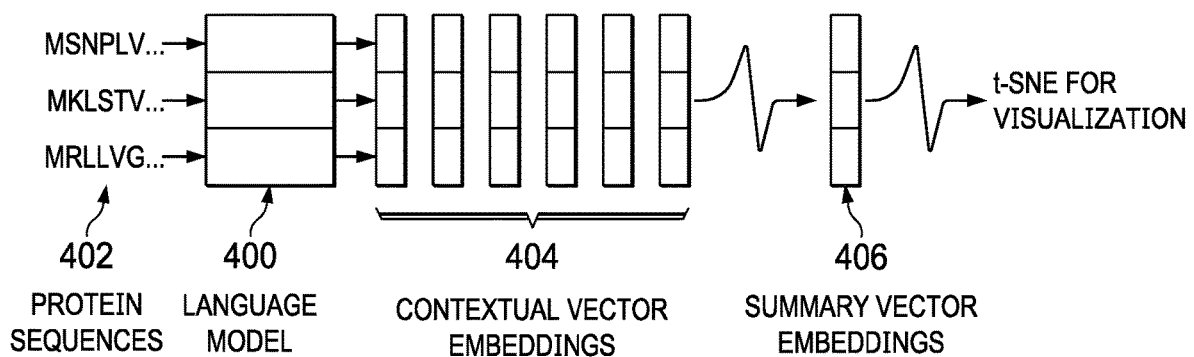
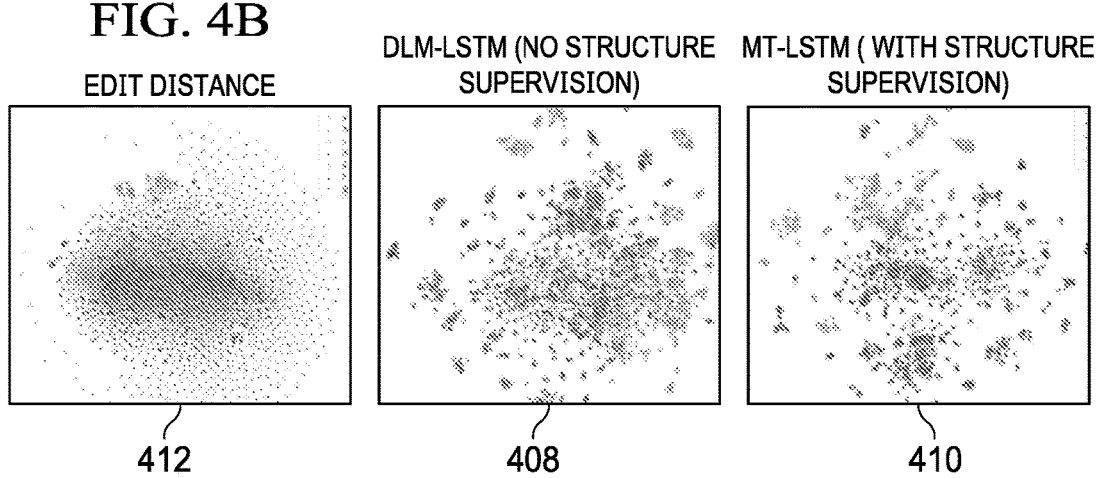

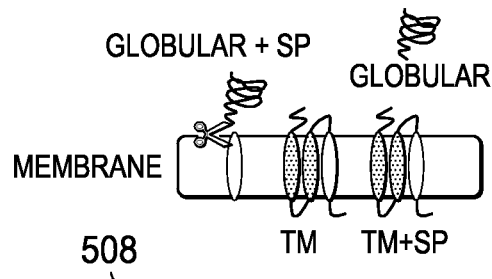
| METHOD | TM | SP+TM | GLOBULAR | GLOBULAR+SP | OVERALL |
|---|---|---|---|---|---|
| TOPCONS | 0.80 | 0.80 | 0.97 | 0.91 | 0.87 |
| PHILIUS | 0.70 | 0.75 | 0.94 | 0.94 | 0.83 |
| PHOBIUS | 0.55 | 0.83 | 0.95 | 0.94 | 0.82 |
| SPOCTOPUS | 0.71 | 0.78 | 0.78 | 0.79 | 0.76 |
| BiLSTM+CRF (MT-LSTM) | 0.88 | 0.90 | 1.00 | 0.96 | 0.93 |
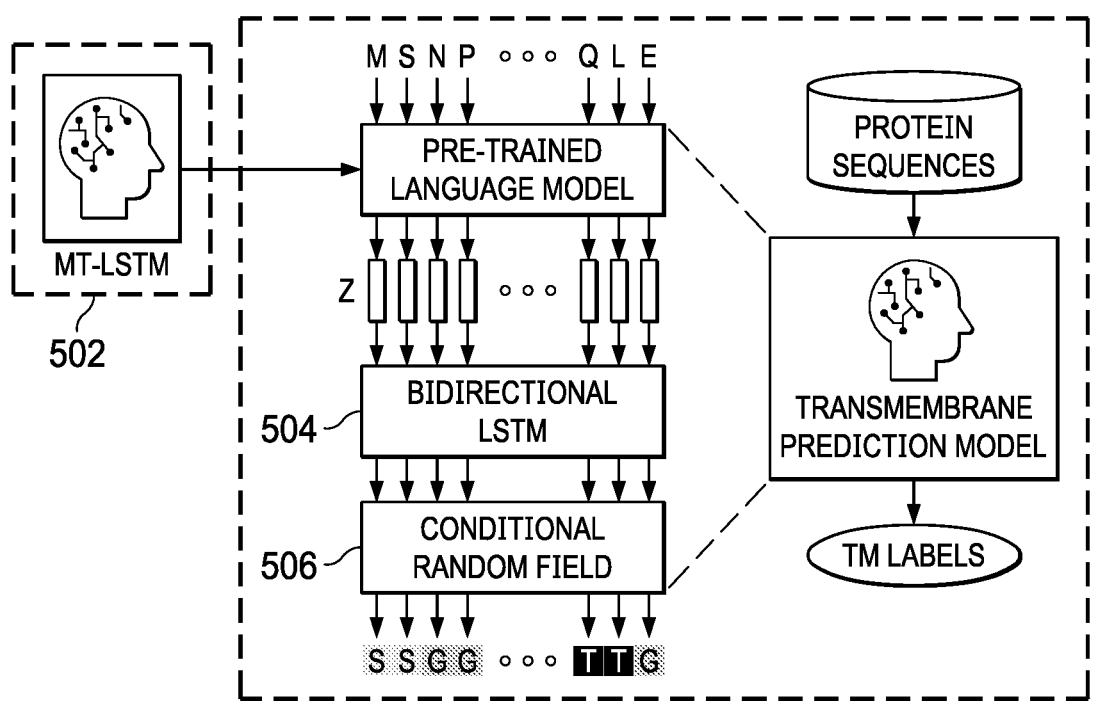
FIG. 5B

- GIVEN AN ALIGNMENT OF THE SEQUENCES:
  - $a_{i,j}=1$ IF POSITION i OF x CORRESPONDS TO POSITION j OF x' AND $a_{i,j}=0$ OTHERWISE
- WE DEFINE THE GLOBAL SIMILARITY BASED ON THE DISTANCE BETWEEN EMBEDDINGS AT MATCHED POSITIONS $$s = \frac{1}{N}\sum_{i=1}^{n}\sum_{j=1}^{m} a_{i,j} \|z_i - z'_j\|$$

$$\text{WHERE } N = \sum_{i=1}^{n}\sum_{j=1}^{m} a_{i,j}$$

1. THE UNNORMALIZED LOG PROBABILITY OF DRAWING AN EDGE FROM $x_i$ TO $x'_j$ IS GIVEN BY $-\|z_i - z'_j\|$ FOR ALL i $$\alpha_{ij} = \frac{e^{-\|z_i - z'_j\|}}{\sum_{k=1}^{n} e^{-\|z_i - z'_k\|}}$$

2. THE UNNORMALIZED LOG PROBABILITY OF DRAWING AN EDGE FROM $x'_j$ TO $x_i$ IS GIVEN BY $-\|z_i - z'_j\|$ FOR ALL j $$\beta_{ij} = \frac{e^{-\|z_i - z'_j\|}}{\sum_{k=1}^{n} e^{-\|z_k - z'_j\|}}$$

3. DEFINE THE SOFT SYMMETRIC ALIGNMENT AS THE PROBABILITY OF DRAWING AN EDGE BETWEEN POSITION i OF X AND POSITION j OF X'

$$\hat{a}_{ij} = \alpha_{ij} + \beta_{ij} - \alpha_{ij}\beta_{ij}$$

FIG. 7

PROTEIN DATABASE SEARCH USING LEARNED REPRESENTATIONS

BACKGROUND

Statement of Federally Sponsored Research or Development

No part of the claimed subject matter was made with government support.

TECHNICAL FIELD

This disclosure relates generally to efficient information search and retrieval methods for searching protein sequences.

RELATED ART

Proteins are molecular machines that carry out the majority of the molecular function of cells. They are composed of linear sequences of amino acids which fold into complex ensembles of 3-dimensional structures, which can range from ordered to disordered and undergo conformational changes; biochemical and cellular functions emerge from protein sequence and structure. Understanding the sequence-structure-function relationship is the central problem of protein biology, and is pivotal for understanding disease mechanisms and designing proteins and drugs for therapeutic and bioengineering applications.

The complexity of the sequence-structure-function relationship continues to challenge computational modeling abilities, in part because existing tools do not realize the potential of the increasing quantity of sequence, structure, and functional information stored in large databases. Until recently, computational methods for analyzing proteins have used either first principles-based structural simulations or statistical sequence modeling approaches that seek to identify sequence patterns that reflect evolutionary, and therefore functional, pressures. Within these methods, structural analysis has been largely first-principles driven while sequence analysis methods are primarily based on statistical sequence models, which make strong assumptions about evolutionary processes, but have become increasingly data driven with the growing amount of available natural sequence information.

Physics-based approaches use all atom energy functions or heuristics designed for proteins to estimate the energy of a given conformation and simulate natural motions. These methods are appealing, because they draw on fundamental understanding of the physics of these systems and generate interpretable hypotheses. Rosetta has been remarkably successful in its use of free energy estimation for protein folding and design, and molecular dynamics software such as GROMACS are widely used for modeling dynamics and fine-grained structure prediction. Rosetta has been especially successful for solving the design problem by using a mix of structural templates and free energy minimization to find sequences that match a target structure. Despite Rosetta's successes, however, it and similar approaches assume simplified energy models, are extremely computationally expensive, require expert knowledge to set up correctly, and have limited accuracy At the other end of the spectrum, statistical sequence models have proven extremely useful for modeling the amino acid sequences of related sets of proteins. These methods allow discovery of constraints on amino acids imposed by evolutionary pressures and are widely used for homology search and for predicting residue-residue contacts in the 3D protein structure using covariation between amino acids at pairs of positions in the sequence (coevolution). Advances in protein structure prediction have been driven by building increasingly large deep learning systems to predict residue-residue distances from sequence families, which culminated recently in the success of AlphaFold2. These methods rely on large datasets of protein sequences that are similar enough to be aligned with high confidence but contain enough divergence to generate statistical signals of covariance. Accordingly, they are unable to learn patterns across large-scale databases of possibly unrelated proteins, and have limited ability to draw on the increasing structure and function information available.

Language models have recently emerged as a powerful paradigm for generative modeling of sequences and as a means to learn "content-aware" data representations from large-scale sequence datasets. Statistical language models are probability distributions over sequences of tokens (e.g., words or characters in natural language processing, amino acids for proteins). Given a sequence of tokens, a language model assigns a probability to the whole sequence. In natural language processing (NLP), language models are widely used for machine translation, question-answering, and information retrieval amongst other applications. In biology, profile HMMs are simple language models that are already widely used for homology modeling and search. Language models are able to capture complex dependencies between amino acids and can be trained on all protein sequences rather than being focused on individual families; in doing so, they have the potential to push the limits of statistical sequence modeling. In bringing these models to biology, it is possible to have the ability to learn from naturally observed sequences, including across all of known sequence space, and also to incorporate existing structural and functional knowledge through multi-task learning. Language models learn the probability of a sequence occurring and this can be directly applied to predict the favorability of sequence mutations. They also learn summary representations, powerful features that can be used to better capture sequence relationships and link sequence to function via transfer learning. Finally, language models also offer the potential for controlled sequence generation by conditioning the language model on structural or functional specifications.

Deep language models are an exciting breakthrough in protein sequence modeling, allowing discovery of aspects of structure and function from only the evolutionary relationships present in a corpus of sequences. The full potential of these models, however, has not been realized as they continue to benefit from more parameters, more compute power, and more data. At the same time, these models can be enriched with strong biological priors through multi-task learning.

BRIEF SUMMARY

The subject matter hereof describes a method for efficient search of protein sequence databases for proteins that have sequence, structural and/or functional homology (with respect to information derived from a search query). Generally, the method involves transforming the protein sequences into vector representations and searching in a vector space. Given a database of protein sequences that is to be searched and a learned embedding model, preferably the database is first pre-processed by applying the embedding model to each amino acid sequence to transform it into a sequence of vector representations. Then, the query sequence is also transformed into a sequence of vector representations, once again preferably using the same learned embedding model. Once the query has been embedded in this manner, proteins are retrieved from the database based on distance between the query embedding and protein embeddings contained with the database. Proteins can be searched for local (i.e., single residue) similarity by indexing and searching embeddings of individual positions. These can be extended to partial or whole protein similarity by aligning sub-sequences or the whole sequence of the query with candidate matches from the database using one or more techniques. Alternatively, whole protein search is performed using fixed-sized vector embeddings representing whole sequences. These can be derived from positive-specific embeddings through, for example, averaging or are directly output by the embedding model. Preferably, rapid and accurate search of the vector space is carried out using one of: (1) exact search using metric data structures (e.g., ball trees or K-D trees), or (2) approximate search using locality sensitive hashing.

The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which:

FIGS. 4A, 4B and 4C depict how the language modeling approach herein is used to capture the semantic organization of proteins; and FIGS. 5A, 5B and 5C depict protein language modeling with transfer learning according to another aspect of this disclosure.

FIG. 7 depicts modeling of global similarity given an alignment of sequences according to an embodiment;

DETAILED DESCRIPTION

Figure 1:
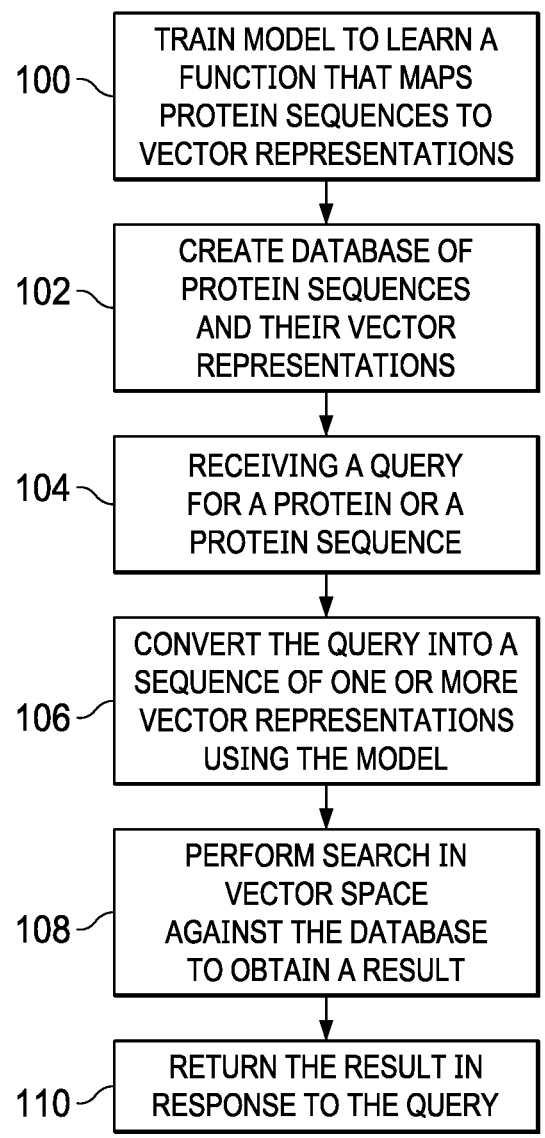
FIG. 1 depicts a high level process flow of a protein database search using learned representations according to this disclosure.

The following describes a method for efficient search of protein sequence databases for proteins that have sequence, structural, and/or functional homology (with respect to information derived from a search query), and according to an embodiment of this disclosure. The method generally involves transforming the protein sequences into vector representations and searching in a vector space. As depicted in the high level process flow in FIG. 1, the method begins at step 100 by training a model to learn a function that maps protein sequences, represented as sequences of amino acids, to sequences of vector representations in a vector space. The model has a set of parameters that are estimated to minimize a loss function over training data. At step 102, a database of protein sequences and their associated sequences of vector representations as determined by the model is created. Steps 100 and 102 typically occur as pre-processing operations. At step 104, and given the database of protein sequences that is to be searched and the learned embedding model, a query for a protein or protein sequence is received. At step 106, the model is used to convert the query into a sequence of one or more vector representations. At step 108, a search is then performed in vector space against the database using the one or more vector representations to obtain a result, the result being obtained in sub-linear or constant time. At step 110, the result is then returned in response to the query.

Thus, a learned embedding model is first trained. Given a database of protein sequences that is to be searched and the learned embedding model, the database is first preprocessed by applying the embedding model to each amino acid sequence to transform it into a sequence of vector representations. Optionally, these can be reduced to a single, fixed size vector for each sequence. Any received query sequence is also transformed into a sequence of vector representations, once again preferably using the same learned embedding model. Once the query has been embedded in this manner, proteins are retrieved from the database based on distance between the query embedding and the protein embeddings contained within the database. Proteins can be searched for local (i.e., single residue) similarity by indexing and searching embeddings of individual positions. These can be extended to partial or whole protein similarity by aligning subsequences or whole sequence of the query with candidate matches from the database using soft-symmetric alignment, optimal transport (e.g., sinkhorn iterations), or Needleman-Wunsch or Smith-Waterman alignments. Alternatively, whole protein search can be performed using fixed-sized vector embeddings representing whole sequences. These can be derived from position-specific embeddings through, for example, averaging or could be directly output by the embedding model. Preferably, there are several methods that can be implemented to perform this search rapidly, namely: (1) exact search using metric data structures (e.g., ball trees or K-D trees), and (2) approximate search using locality sensitive hashing.

In the first search method, exact database search is performed in sub-linear time (O(log N), where N is the size of the database) using metric data structures to store database proteins by their vector embeddings. Metric data structures are trees that allow for efficient k-nearest neighbors search by taking advantage of the triangle inequality to prune data points that cannot be close to the query. These methods first pre-process the database into a tree structure such that each subtree contains smaller and smaller partitions of the metric space. This allows search to be performed in sublinear time, because the subtree in which a query belongs is identified at each level and all data points in the database are pruned from the search. The exact search approach allows similar proteins to a query protein to be retrieved by finding the nearest proteins in embedding space. Preferably, nearness is defined by the choice of distance metric and can include, but is not limited to, Euclidean, Manhattan, and Cosine distances. In an example of this approach, the database is pre-processed by organizing the embedded proteins into a search tree. In a K-D tree, this is achieved by iteratively partitioning the embedding space with hyperplanes and in a ball tree space is divided into hyperspheres. This data structure preferably uses binary splits or multi-way splits as in M-trees, although this is not a limitation. Additional efficiency is achieved by applying dimensionality reduction, for example principle components analysis or random projection, to the protein vector embeddings. Depending on implementation strategy, speed and accuracy are traded off, e.g., by adjusting the dimensionality of the reduced embeddings.

In the second method, search efficiency is facilitated by locality sensitive hashing. In this scheme, proteins are placed into indexed buckets based on approximate location in embedding space. These buckets can be defined by random linear partitions of the embedding space or some other scheme defined by a fixed set of hash functions. Then, and given a query protein, similar proteins are retrieved in constant time by applying the hash functions to the query protein embeddings, and then returning all database proteins found in the same buckets. Optionally, these results are refined using direct distance comparison.

An alternative to using locality sensitive hashing for approximate search uses proximity graph methods, such as hierarchical, navigable small-world (HNSW).

The Learned Embedding Model

The following provides high level details of how the learned embedding model is derived. This process provides for the deep contextual protein sequence embeddings that are learned from sequence and structure.

In particular, the approach herein learns a function that maps protein sequences, represented as sequences of amino acids, to sequences of vector representation, preferably using multiple sources of feedback. This function accepts a sequence as input and outputs a sequence of distributed vector representations, preferably one per position of the input. This function is parameterized as a deep neural network (DNN) that can be composed of, but is not limited to, one or more layers of recurrent neural networks (e.g., LSTM, GRU), transformers, or convolutional neural networks. The parameters of this model are estimated using stochastic gradient descent (or a derivative thereof) to minimize a loss function over the training data. Typically, the loss function is composed of three parts: (1) a denoising/masked language modeling term, (2) a structural similarity metric embedding term, and (3) a residue-residue contact prediction term. The following provides additional details of these terms, according to one embodiment.

The denoising/masked language model objective is the negative log-likelihood of the amino acids at randomly masked positions in the protein sequence given the rest of the amino acids in the sequence. Preferably, this is calculated by randomly replacing amino acids in an input sequence with a token drawn from a background noise distribution (for denoising) or a mask token (for masked). These noised/masked sequences are processed with the embedding function to give one vector representation per position (in a preferred embodiment). These vector representations are then passed through a learned linear transformation, which outputs the predicted log probability of the amino acids at each position of the sequence. The negative log-likelihood is averaged over the noised/masked positions giving the denoising/masked language modeling loss function.

The structural similarity metric embedding term preferably is derived as follows. Given a set of protein sequences classified into a structural hierarchy (e.g., as in a structural classification of proteins (SCOP) or the CATH protein structure database), the structural similarity metric embedding loss measures the ability to predict structural similarity between pairs of proteins based on their vector embeddings. Given two protein sequences, this is calculated by first embedding each protein into a sequence of vector representations. These sequences of vector representations are then aligned using a soft symmetric alignment approach to calculate an alignment score between the proteins in embedding space. This score is then used to calculate the probability of each similarity level between the two proteins using an ordinal regression layer with jointly learned parameters. The negative log-likelihood of the ground truth similarity is the structural similarity metric embedding loss.

The final source of training signal is the residue-residue contact prediction term, which preferably is derived as follows. Given a protein structure, the distances between residues in 3D space define the residue-residue distance map. Thresholding this map at a fixed distance cutoff, typically 8 Angstroms, yields a binary residue-residue contact map. This map is an L by L matrix, where L is the length of the sequence, ones for i, j residue pairs that are within the distance threshold and zeros otherwise. These contacts are predicted from vector embeddings, preferably using a contact prediction module. This module is a function with learned parameters that accepts a sequence of vector representations and returns an L by L matrix where each entry is the predicted log likelihood ratio that the $i^{th}$ and $j^{th}$ residues are within the distance threshold. This module can be composed of a function to calculate a pairwise feature vector for every residue $i^{th}$, $j^{th}$ pair followed by convolutional neural network layers or can be a linear projection of the embeddings into an L×D matrix followed by the dot product of these embeddings with themselves to yield a final L×L prediction matrix. Preferably, the contact prediction term is the negative log likelihood of the ground truth contacts given by the predicted contact probabilities.

Preferably, the complete loss function is a weighted sum of the three individual loss terms. In one implementation, these weights are hyperparameters that are chosen to assign the desired strength to each loss term. The weights can be used to select individual loss terms when the other terms are set to zero. The gradient of this combined loss with respect to the model parameters is calculated using the back propagation algorithm in order to update the model parameters.

Thus, in this approach to deriving the learned embedding model, one neural network with one set of parameters is used for all tasks and is trained simultaneously.

The following sections describe a representative implementation.

Glossary

The following terms used herein have the following meaning:

"1-hot [embedding]" is a vector representation of a discrete variable commonly used for discrete values that have no meaningful ordering. Each token is transformed into a V-dimensional zero vector, where V is the size of the vocabulary (the number of unique tokens, e.g., 20, 21, or 26 for amino acids depending on inclusion of missing and non-canonical amino acid tokens), except for the index representing the token, which is set to one.

"autoregressive [language model]" is a language model that factorizes the probability of a sequence into a product of conditional probabilities in which the probability of each token is conditioned on the preceding tokens, $p(x_1 \ldots x_L) = \Pi_{i=1}^{L} p(x_i | x_1 \ldots x_{i-1})$. Examples of autoregressive language models include k-mer (also known as n-gram) models, Hidden Markov Models, and typical autoregressive recurrent neural network or generative transformer language models. These models are called autoregressive because they model the probability of one token after another in order.

"bilinear projection layer" is a deep learning layer that projects two vectors into a third vector space using a learned linear projection, i.e., $y=xWz+b$, where y is the output vector, x and z are input vectors, and W and b are learnable parameters. As described below, this layer is applied as the output layer for predicting contacts between residues at position i and j.

"doze task" is a task in natural language processing, also known as the doze test. The task is to fill in missing words given the context. For example, "The quick brown ___ jumps over the lazy dog."

A "conditional random field" models the probability of a set (sequence in this case, i.e., linear chain CRF) of labels given a set of input variables by factorizing it into locally conditioned potentials conditioned on the input variables, $p(y_1 \ldots y_L|x_1 \ldots x_L)=p(y_1|x_1 \ldots x_L) \prod_{i=2}^{L} p(y_i|y_{i-1}, x_1 \ldots x_L)$. This is often simplified such that each conditional only depends on the local input variable, i.e., $p(y_1 \ldots y_L| x_1 \ldots x_L)=p(y_1|x_1)\prod_{i=2}^{L} p(y_i|y_{i-1},x_i)$. Linear chain CRFs can be seen as the discriminative version of Hidden Markov Models.

A "contextual vector embedding" is a vector embedding that includes information about the sequence context in which a token occurs. Encoding context into vector embeddings is important in Natural Language Processing (NLP) because words can have different meanings in different contexts (i.e., many homonyms exist). In the case of proteins, this problem is exacerbated, because there are only 20 (canonical) amino acids and so their "meaning" is highly context dependent. This is in contrast to typical vector embedding methods that learn a single vector embedding per token regardless of context.

A "distributional hypothesis" is an observation that words that occur in similar contexts tend to have similar meanings. This hypothesis applies also to proteins due to evolutionary pressure.

"few-shot learning" refers to the problem of learning a predictive model, usually a classifier, with very few examples from each class. One-shot learning is a special case of few-shot learning where only one example is given. This problem requires rapid specialization to new datasets and labeled classes.

A "generative model" is a of the data distribution, $p(X)$, joint data distribution, $p(X, Y)$, or conditional data distribution, $p(X|Y=y)$. It is usually framed in contrast to discriminative models that model the probability of the target given an observation, $p(Y|X=x)$. Here, X is observable, for example the protein sequence, and Y is a target that is not observed, for example the protein structure or function. Conditional generative and discriminative models are related by Bayes' theorem. Language models are generative models.

A "hidden layer" is an intermediate vector representations in a deep neural network. Deep neural networks are structured as layered data transformations before outputting a final prediction. The intermediate layers are referred to as "hidden" layers.

"inductive bias" describes the assumptions that a model uses to make predictions for data points it has not seen. That is, the inductive bias of a model is how that model generalizes to new data. Every machine learning model has inductive biases, implicitly or explicitly.

A "language model" is a probabilistic model of whole sequences. In the case of natural language, language models typically describe the probability of sentences or documents. In the case of proteins, they model the probability of amino acid sequences. Being simply probabilistic models, language models can take on many specific incarnations from column frequencies in multiple sequence alignments to Hidden Markov Models to Potts models to deep neural networks.

"manifold embedding" refers to a distance preserving, low dimensional embedding of data. The goal of manifold embedding is to find points low dimensional vectors, $z_1 \ldots z_n$, such that the distances, $d(z_i,z_j)$, are as close as possible to the distances in the original data space, $d(x_i,x_j)$, given n high dimensional data vectors, $x_1 \ldots x_n$. t-SNE is a commonly used manifold embedding approach for visualization of high dimensional data.

A "masked language model" refers to a training task used by BERT and other recent bidirectional language models. Instead of modeling the probability of a sequence autoregressively, masked language models seek to model the probability of each token given all other tokens. For computational convenience, this is achieved by randomly masking some percentage of the tokens in each minibatch and training the model to recover those tokens. An auxiliary token is added to the vocabulary to indicate that this token has been masked.

"meta learning," also referred to as "learning to learn," is the problem of learning a system that is designed to rapidly adapt to new tasks or data domains.

"multi-task learning" is a machine learning paradigm in which multiple tasks are learned simultaneously. The idea is that similarities between tasks can lead to each task being learned better in combination rather than learning each individually. In the case of representation learning, multi-task learning can also be useful for learning representations that encode information relevant for all tasks. Multi-task learning allows use of signals encoded in other training signals as an inductive bias when learning a goal task.

"representation learning" refers to the problem of learning features, or intermediate data representations, better suited for solving a prediction problem on raw data. Deep learning systems are described as representation learning systems, because they learn a series of data transformations that make the goal task progressively easier to solve before outputting a prediction.

"self-supervised learning" refers to methods for learning from data without labels. Generally, the term is used to describe methods that automatically create labels through data augmentation or generative modeling. This type of learning can be viewed as a subset of unsupervised learning focused on learning representations useful for transfer learning.

"semantic priors" refers to a prior semantic understanding of a word or token, e.g., protein structure or function.

"semantics" is the meaning of a word or token. In reference to proteins, the term refers to the "functional" purpose of a residue, or combinations of residues.

"supervised learning" is a problem in machine learning, in particular, how to learn a function to predict a target variable, usually denoted y, given an observed one, usually denoted x, from a set of known x, y pairs.

"transfer learning" is a type of machine learning problem, in particular, how to take knowledge learned from one task and apply it to solve another related task. When the tasks are different but related, representations learned on one task can be applied to the other. For example, representations learned from recognizing dogs could be transferred to recognizing cats. In the case of proteins and language models, knowledge gained from learning is applied to generate sequences to predicting function. Transfer learning may also be used to apply representations learned from predicting structure to function or from predicting one function to another function among other applications.

"unsupervised learning" is a problem in machine learning that asks how to learn patterns from unlabeled data. Clustering is a classic unsupervised learning problem. Unsupervised learning is often formulated as a generative modeling problem, where data is viewed as being generated from some unobserved latent variable(s) that are inferred jointly with the parameters of the model.

"vector embedding" is a term used to describe multidimensional real numbered representations of data that is usually discrete or high dimensional, word embeddings being a classic example. Vector embeddings are sometimes referred to as "distributed vector embeddings" or "manifold embeddings" or simply just "embeddings." Low-dimensional vector representations of high dimensional data such as images or gene expression vectors as found by methods such as t-SNE are also vector embeddings. Usually, the goal in learning vector embeddings is to capture some semantic similarity between data as a function of similarity or distance in the vector embedding space.

Protein Language Models

Figure 2A:
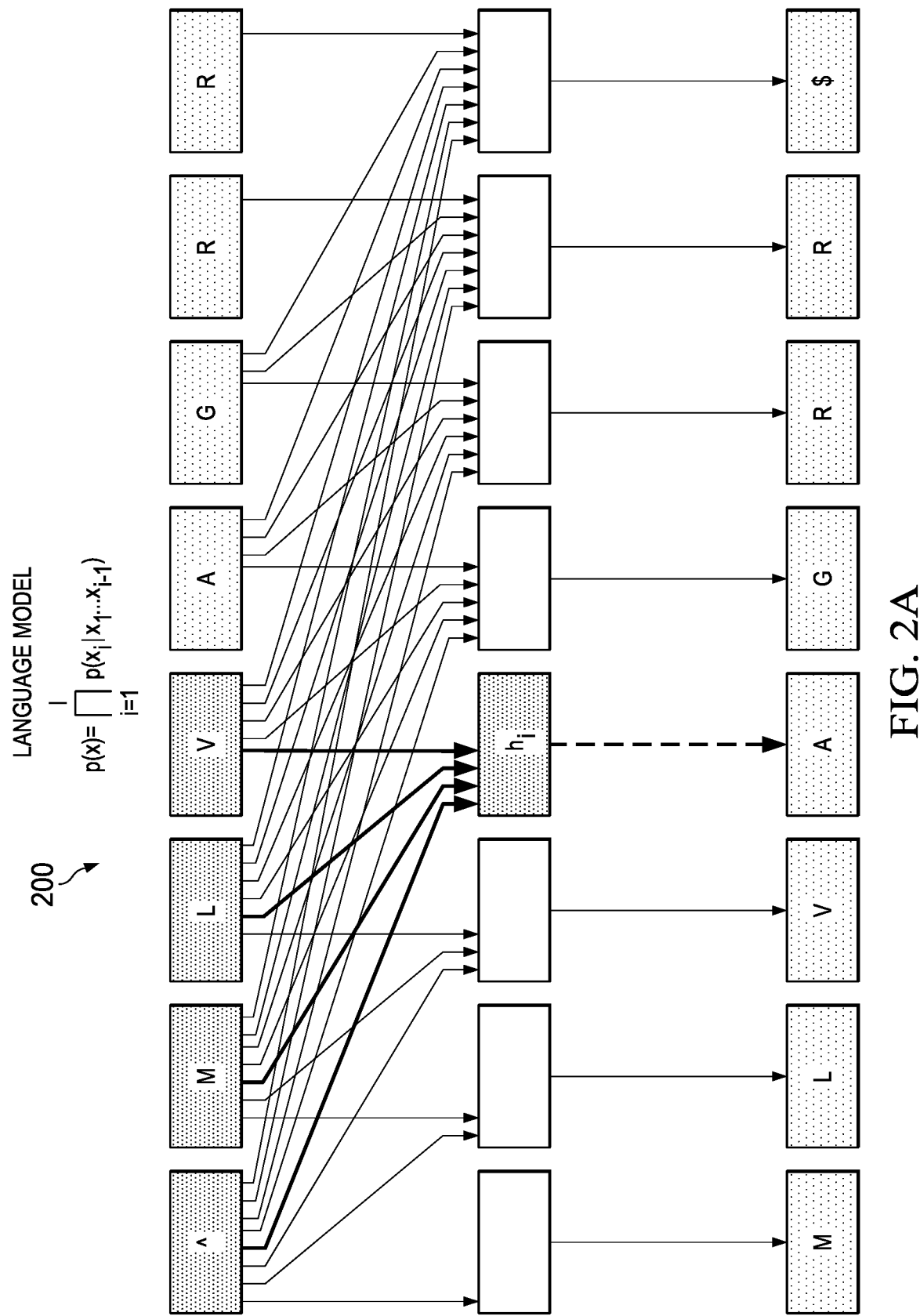
FIGS. 2A, 2B and 2C depict known language model architectures and language modeling approaches.
Figure 2B:
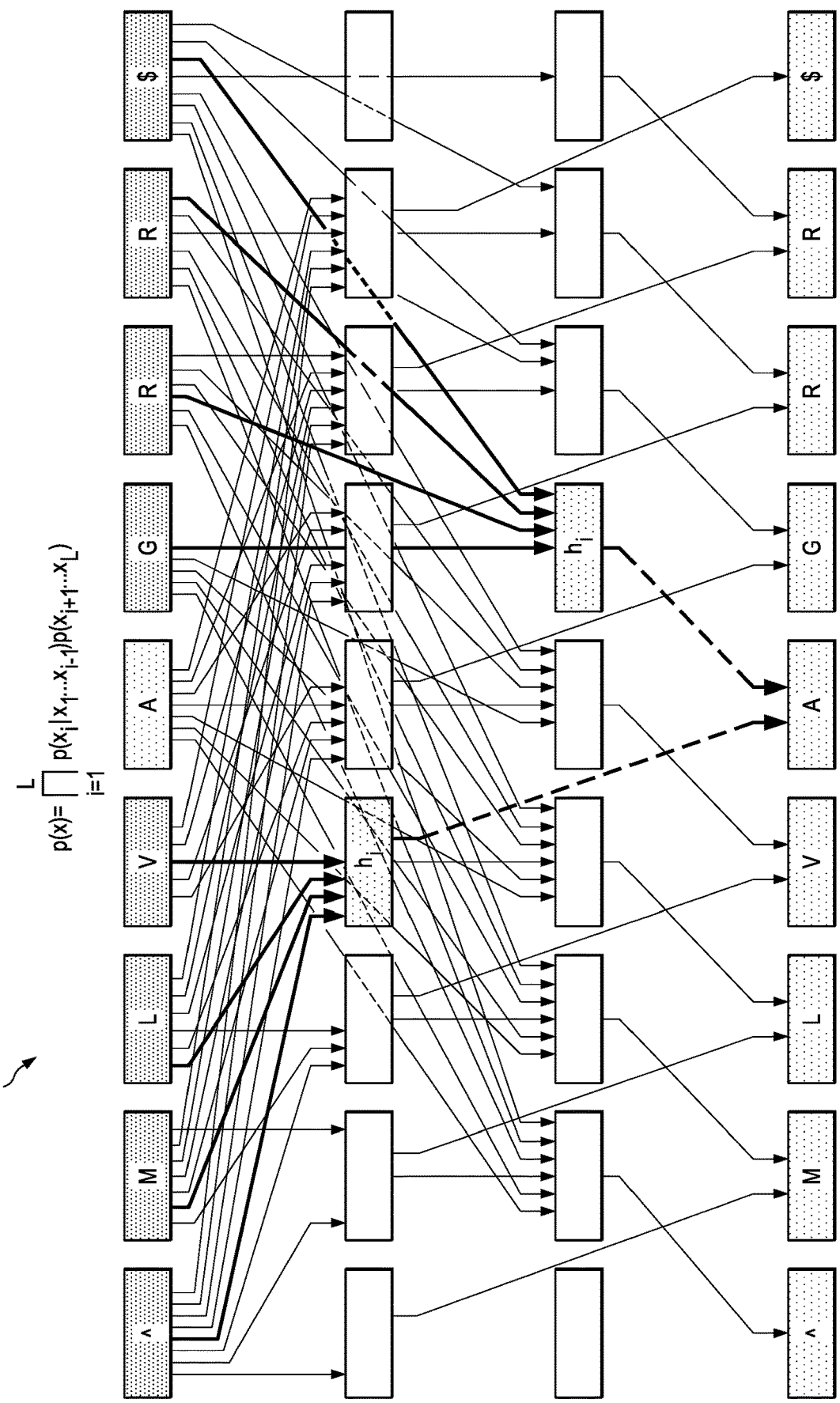
Figure 2C:
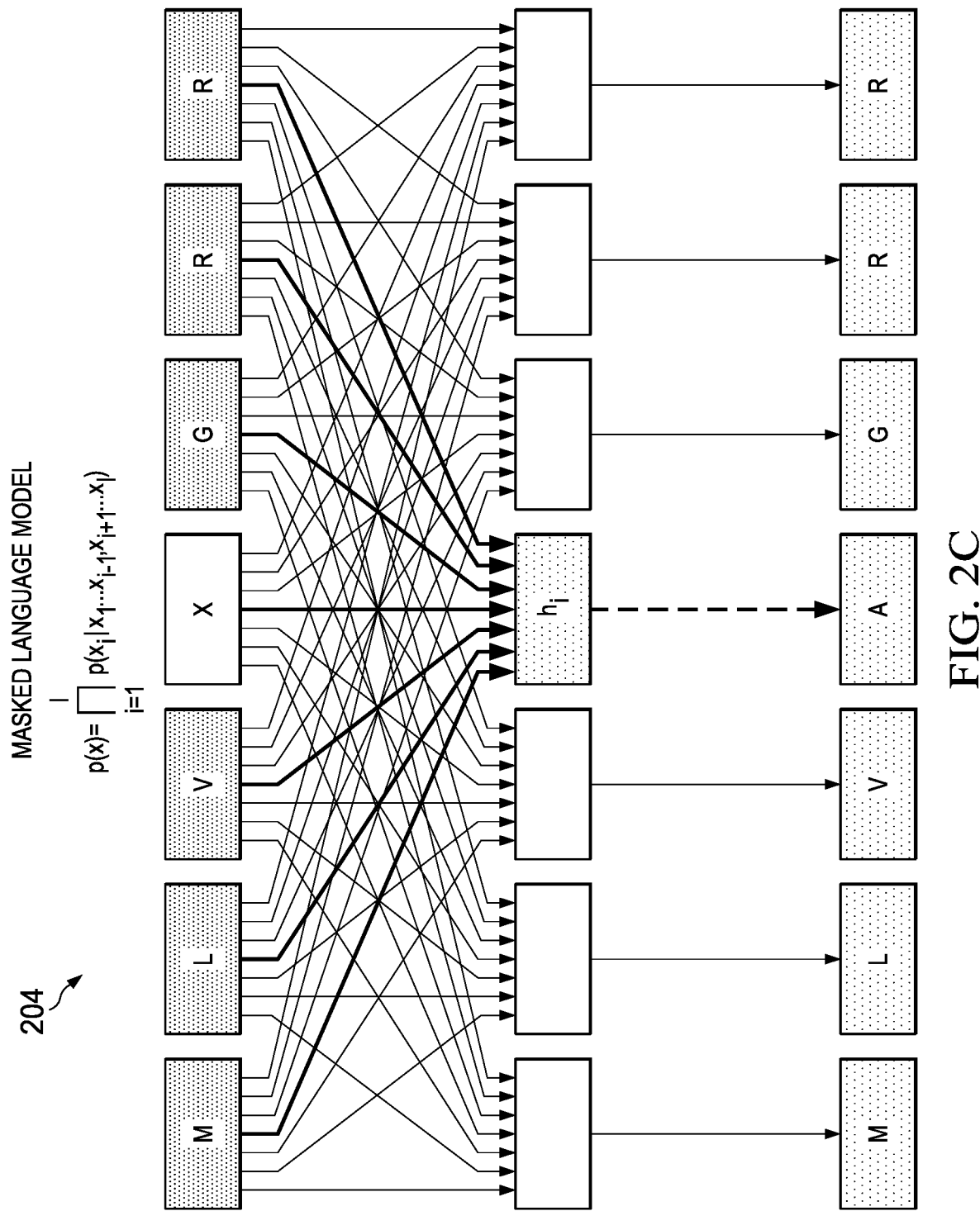

FIGS. 2A, 2B and 2C depict several examples of known language model architectures. As noted above, language models model the probability of sequences. Typically, this distribution is factorized over the sequence such that the probability of a token (e.g., amino acid) at position i ($x_i$) is conditioned on the previous tokens. In a simple neural language model, such as model 200 in FIG. 2A, this is achieved by first computing a hidden layer ($h_i$) given by the sequence up to position i-1 and then calculating the probability distribution over token $x_i$ given $h_i$. In this example sequence, "Λ" and "$" represent start and stop tokens respectively, and the sequence has length L. Model 202 in FIG. 2B is a bidirectional language model that models the probability of a token conditioned on the previous and following tokens independently. For each token $x_i$, a hidden layer is computed using separate forward and reverse direction models. These hidden layers are then used to calculate the probability distribution over tokens at position i conditioned on all other tokens in the sequence. This allows for extracting representations that capture complete sequence context. Model 204 in FIG. 2C is a masked language model that models probability of tokens at each position conditioned on all other tokens in the sequence and, in particular, by replacing the token at each position with an extra "mask" token ("X"). In model 204, the hidden layer at each position is calculated from all tokens in the sequence which allows the model to capture conditional non-independence between tokens on either side of the masked token. This formulation lends itself well to learning representations useful for transfer learning, because the representations can depend on the full context of each token.

The language models for protein sequence representation learning as depicted in FIG. 2 FIGS. 2A, 2B and 2C have seen a surge of interest following the success of large-scale models in the field of natural language processing (NLP). These models draw on the idea that distributed vector representations of proteins can be extracted from generative models of protein sequences, learned from a large and diverse database of sequences across natural protein space, and thus can capture the semantics, or function, of a given sequence. Here, function refers to any and all properties related to what a protein does. These properties are often subject to evolutionary pressures because these functions must be maintained or enhanced for an organism to survive and reproduce. These pressures manifest in the distribution over amino acids present in natural protein sequences and, hence, are discoverable from large and diverse enough sets of naturally occurring sequences.

The ability to learn semantics emerges from the distributional hypothesis: tokens (e.g., words, amino acids) that occur in similar contexts tend to carry similar meanings. Language models only require sequences to be observed and are trained to model the probability distribution over amino acids using an autoregressive formulation (models 200 and 202) or masked position prediction formulation (model 204, also called a cloze task in NLP). In autoregressive language models, the probability of a sequence is factorized such that the probability of each token is conditioned only on the preceding tokens. This factorization is exact and is useful when sampling from the distribution or evaluating the probabilities themselves is of primary interest. The drawback to this formulation is that the representations learned for each position depend only on preceding positions, potentially making them less useful as contextual representations. The masked position prediction formulation (also known as masked language modeling) addresses this problem by considering the probability distribution over each token at each position conditioned on all other tokens in the sequence. This bidirectional approach does not allow calculating correctly normalized probabilities, but is more appropriate when the learned representations are the outcomes of primary interest. The unprecedented recent success of language models in natural language processing, e.g., Google® BERT and OpenAI GTP-3, is largely driven by their ability to learn from billions of text entries in enormous online corpora. Analogously, there are natural protein sequence databases with hundreds of millions of unique sequences that continue to grow rapidly.

Recent advances in NLP have been driven by innovations in neural network architectures, new training approaches, increasing compute power, and increasing accessibility of huge text corpuses. Several NLP methods have been proposed that draw on unsupervised, now often called self-supervised, learning to fit large-scale bidirectional long-short term recurrent neural networks (bidirectional LSTMs or biLSTMs), or transformers and its recent variants. LSTMs are recurrent neural networks. These models process sequences one token at a time in order and therefore learn representations that capture information from a position and all previous positions. To include information from tokens before and after any given position, bidirectional LSTMs combine two separate LSTMs operating in the forward and backward directions in each layer (model 202). Although these models are able to learn representations including whole sequence context, their ability to learn distant dependencies is limited in practice. To address this limitation, transformers learn representations by explicitly calculating an attention vector over each position in the sequence. In the self-attention mechanism, the representation for each position is learned by "attending to" each position of the same sequence, well suited for masked language modeling (model 204), but transformers are widely used as autoregressive language models as well. The attention mechanism allows transformers to easily learn dependencies between positions of arbitrary distance.

In natural language processing, it has been recognized that the hidden layers (intermediate representations of stack neural networks) of biLSTMs encode semantic meaning of words in context. This observation has been newly leveraged for biological sequence analysis to learn more semantically meaningful sequence representations. The success of deep transformers for machine translation inspired their application to contextual text embedding, that is learning contextual vector embeddings of words and sentences, giving rise to the now widely used Bidirectional Encoder Representations from Transformers (BERT) model in NLP. BERT is a deep transformer trained as a masked language model on large text corpora. As a result, it learns contextual representations of text that capture contextual meaning and improve the accuracy of downstream NLP systems. Transformers have also demonstrated impressive performance as autoregressive language models, for example, with the Generative Pre-trained Transformer (GPT) family of models, which are useful in natural language generation. These uses have inspired subsequent applications to protein sequences.

Although transformers are powerful models, they require enormous numbers of parameters and train more slowly than typical recurrent neural networks. With massive scale datasets and compute and time budgets, transformers can achieve useful results but, generally, recurrent neural networks (e.g., biLSTMs) need less training data and less compute, so are more suitable for problems where fewer sequences are available, such as training on individual protein families, or where compute budgets are constraining. Constructing language models that achieve high accuracy with better compute efficiency is an algorithmic challenge for the field. An advantage of general purpose pre-trained protein models is that there is only a need to do the training step (which is often expensive) once; the models can then be used to make predictions or can be applied to new problems via transfer learning, as discussed below.

Using these and other tools, protein language models are able to synthesize the enormous quantity of known protein sequences by training on hundreds of millions of sequences stored in protein databases (e.g., UniProt, Pfam, NCBI). The distribution over sequences learned by language models captures the evolutionary fitness landscape of known proteins. When trained on tens of thousands of evolutionarily related proteins, the learned probability mass function describing the empirical distribution over naturally occurring sequences has shown promise for predicting the fitness of sequence variants. Because these models learn from evolutionary data directly, they are able to make accurate predictions about protein function when function is reflected in the fitness of natural sequences. Indeed, it has been demonstrated that language models fit on individual protein families are accurate predictors of variant fitness measured in deep mutational scanning datasets. Recent work has since shown that the representations learned by language models are also powerful features for learning of variant fitness as a subsequent supervised learning task, building on earlier observations that language models can improve protein property prediction through transfer learning.

A number of other works have focused on increasing the scale of these models by adding more parameters and more learnable layers to improve sequence modeling. Interestingly, because so many sequences are available, these models continue to benefit from increased size. This parallels the general trend in natural language processing, where the number of parameters, rather than specific architectural choices, is the best indicator of model performance. Ultimately, however, model size is limited by the computational resources available to train and apply these models. In NLP, models such as BERT and GPT-3 have become so large that only the best funded organizations with massive Graphics Processing Unit (GPU) compute clusters are realistically able to train and deploy them. This is demonstrated in some recent work on protein models where single transformer-based models were trained for days to weeks on hundreds of GPUs, costing potentially hundreds of thousands of dollars for training. Increasing the scale of these models promises to continue to improve our ability to model proteins, but more resource efficient algorithms are needed to make these models more accessible to the broader scientific community.

The language models discussed above and depicted in FIG. 2 natural protein sequence information. They do not learn from the protein structure and function knowledge, e.g., that has been accumulated over the past decades of protein research. Incorporating such knowledge requires supervised approaches, as is now described in more detail below.

Supervision Encodes Biological Meaning

Proteins are more than sequences of characters: they are physical chains of amino acids that fold into three-dimensional structures and carry out functions based on those structures. The sequence-structure-function relationship is the central pillar of protein biology and significant time and effort has been spent to elucidate this relationship for select proteins of interest. In particular, the increasing throughput and ease-of-use of protein structure determination methods (e.g., x-ray crystallography and cryo-EM), has driven a rapid increase in the number of known protein structures available in databases such as the Protein Data Bank (PDB). There are over 175,000 entries in PDB, and this number is growing rapidly. 14,000 new structures were deposited in 2020 and the rate of new structure deposition is increasing. As will be seen, the techniques herein leverage the intuition that incorporating such knowledge into training the models via supervised learning aids in predicting function from sequence, entirely bypassing the step of solving structure.

As noted above, supervised learning is the problem of finding a mathematical function to predict a target variable given some observed variables. In the case of proteins, supervised learning is commonly used to predict protein structure from sequence, protein function from sequence, or for other sequence annotation problems (e.g., signal peptide or transmembrane region annotation). Beyond making predictions, supervised learning also can be used to encode specific semantics into learned representations.

As will be seen, when supervised approaches are used, semantic priors are encoded into the models. These priors are valuable for learning relationships that are not apparent from the raw data. For example, unrelated protein sequences can form the same structural fold and, therefore, are semantically similar. This relationship, however, cannot be deduced from sequence alone. Supervision is required to learn that these sequences belong to the same semantic category. Although structure is more informative of function than sequence, and structure is encoded by sequence, predicting structure remains hard, particularly due to the relative paucity of structural relative to sequence data.

Evolutionary relationships between sequences are informative of structural and functional relationships, but only when the degree of sequence homology is sufficiently high. Above 30% sequence identity, structure and function are usually conserved between natural proteins. Often called the "twilight zone" of protein sequence homology, proteins with similar structures and functions still exist below this level, but they can no longer be detected from sequence similarity alone, and it is unclear whether their functions are conserved. Although it is generally believed that proteins with similar sequences form similar structures, there are also interesting examples of highly similar protein sequences having radically different structures and functions and of sequences that can form multiple folds. Evolutionary innovation requires that protein function can change with only a few mutations. Furthermore, although structure and function are related, they should not be directly conflated.

These phenomena suggest that there are aspects of protein biology that may not be discoverable by statistical sequence models alone. Supervision that represents known protein structure, function, and other prior knowledge may be necessary to encode distant sequence relationships into learned embeddings. By analogy, cars and boats are both means of transportation, but one would not expect a generative image model to infer this relationship from still images alone. These relationships, however, can be taught through supervision.

On this premise, the techniques here are premised on the notion that incorporating structural supervision when training a protein language model improves ability to predict function in downstream tasks through transfer learning.

Multi-Task Language Models

Figure 3A:
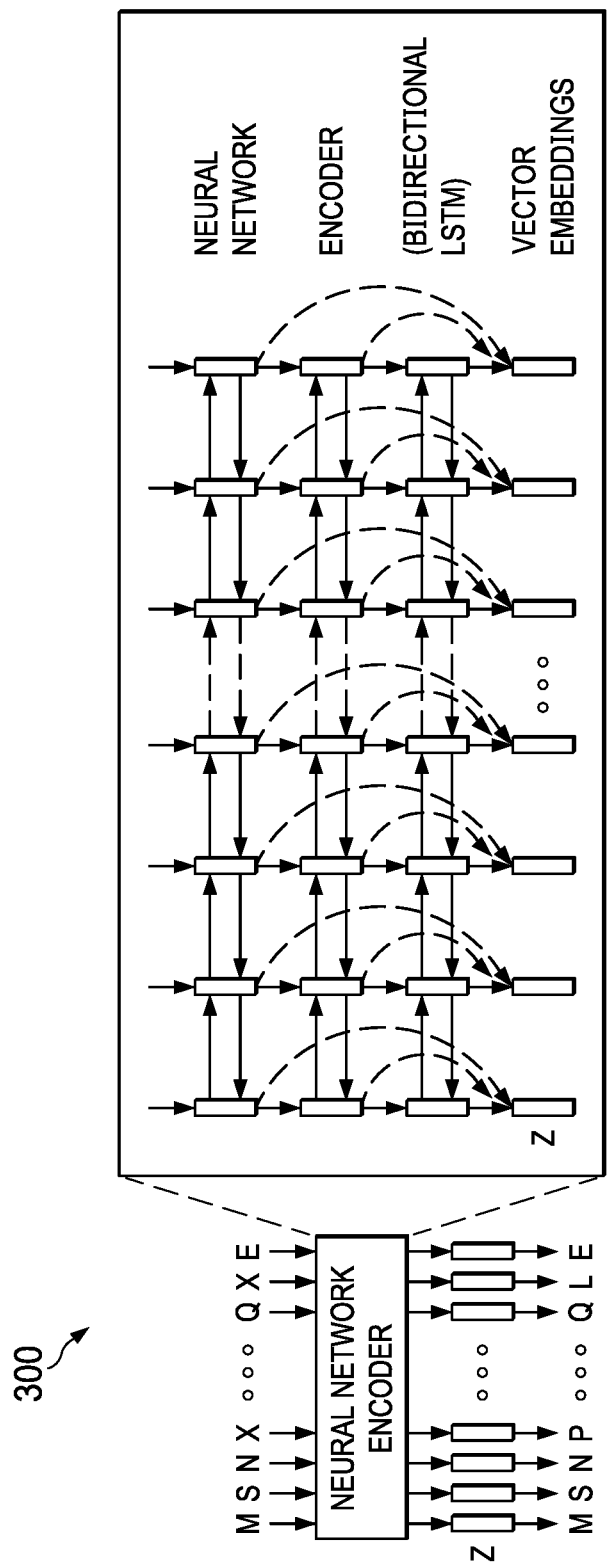
FIGS. 3A, 3B and 3C depict a multi-task contextual embedding model learning framework of this disclosure.
Figure 3B:
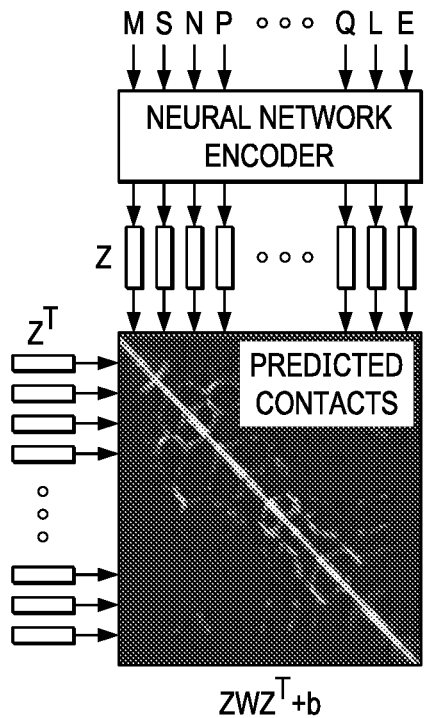
Figure 3C:
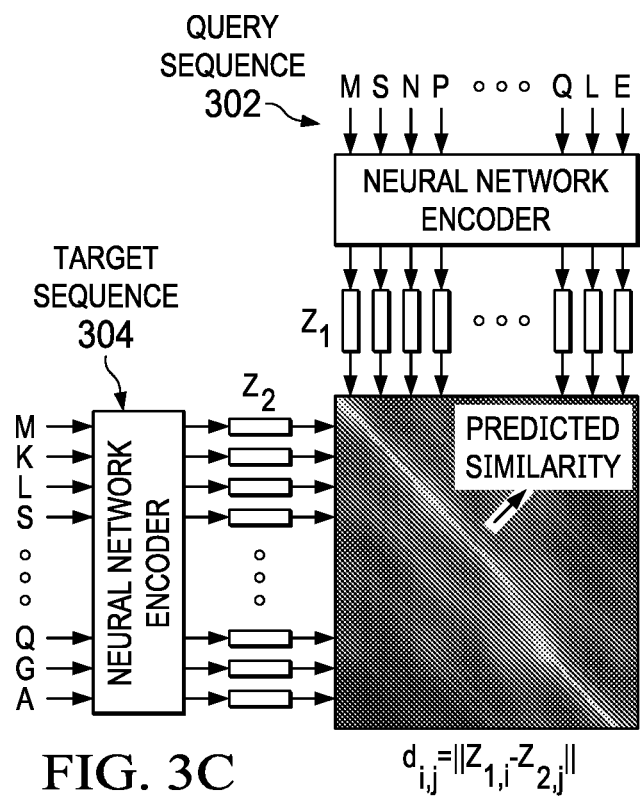

FIGS. 3A, 3B and 3C depict a multi-task contextual embedding model learning framework according to an illustrative embodiment. As depicted in FIG. 3A, a neural network (NN) sequence encoder 300 is trained to solve several (e.g., three (3)) tasks simultaneously. The encoder is a bidirectional LSTM. The first task is masked language modeling, e.g., on large numbers (e.g., millions) of natural protein sequences. Preferably, two sources of structural supervision in a multi-task framework (MT-LSTM for Multi-Task LSTM) are included to encode structural semantics directly into the representations learned by the language model. This is combined with the masked language model objective to benefit from evolutionary and less available structure information (typically, only tens of thousands of proteins). The masked language model objective allows the language model to learn contextual embeddings from hundreds of millions of sequences. This training framework is agnostic to the neural network (NN) architecture, but preferably the three layer bidirectional LSTM 300 with skip connections is used to capture long range dependencies but train quickly. A skilled person will recognize that one can train language models using only this objective (DLM-LSTM), but can also enrich the model with structural supervision. As depicted in FIG. 3B, a first structure task is performed using the model. This task predicts contacts between residues in protein structures using a bilinear projection of the learned embeddings. In this task, the hidden layer representations of the language model are then used to predict residue-residue contacts using a bilinear projection, i.e., the approach models the log likelihood ratio of a contact between the i-th and j-th residues in the protein sequence, by $z_i W z_j + b$, where matrix W and scalar b are learned parameters. As depicted at FIG. 3C, a second source of structural supervision is structural similarity, preferably as defined by the Structural Classification of Proteins (SCOP) hierarchy. The task predicts the ordinal levels of similarity between pairs of proteins by aligning the sequences in embedding space. This embeds the query 302 and target 304 sequences using the language model ($Z_1$ and $Z_2$); it then predicts the structural homology by calculating the pairwise distances between the query and target embeddings ($d_{i,j}$) and aligning the sequences based on these distances.

More specifically, and in the embodiment depicted in FIGS. 3A, 3B and 3C, protein language models are trained with self-supervision on a large amount of natural sequence data and with structure supervision on a smaller set of sequence, structure pairs, thereby enriching the learned representations. This training approach provides significant improvements in downstream prediction. In a practical implementation, a dataset that contains 76 million protein sequences from Uniref and an additional 28,000 protein sequences with structures from SCOP was generated. Next, and as depicted in FIG. 3A, the bidirectional LSTM 300 was trained with three learning tasks simultaneously, namely: (a) the masked language modeling task; (b) the residue-residue contact prediction, and (c) the structural similarity prediction. The fundamental notion behind this training scheme is to combine self-supervised and supervised learning approaches to overcome the shortcomings of each. Specifically, the masked language modeling objective (self-supervision) allows the model to learn from millions of natural protein sequences (e.g., from Uniprot). This learning, however, does not include any prior semantic knowledge from protein structure and, therefore, has difficulty learning semantic similarity between divergent sequences. To address this, the two structural supervision tasks (residue-residue contact prediction and structural similarity prediction) are then leveraged, preferably training with tens of thousands of protein structures classified by SCOP. As noted above, in the residue-residue prediction task, the hidden layers of the language model are used to predict contacts between residues within the 3D structure, preferably using a learned bilinear projection layer. In the structural similarity prediction task, the hidden layers of the language model are used o predict the number of shared structural levels in the SCOP hierarchy, preferably by aligning the proteins in vector embedding space and using this alignment score to predict structural similarity from the sequence embeddings. The parameters of the language model are shared across the self-supervised and two supervised tasks and the entire model is trained end-to-end. The set of proteins with known structure is much smaller than the full set of known proteins in Uniprot and, therefore, by combining these tasks in a multi-task learning approach as described above, the system learns language models and sequence representations that are enriched with strong biological priors from known protein structures. This model is sometimes referred to herein as the MT-(multi-task-) LSTM.

Training Methods

The following provides additional details regarding preferred methods for implementing the above-described training. As noted above, preferably the sequence encoder of the language model herein (DLM- or in the preferred embodiment, MT-LSTM) is structured as a three-layered bidirectional LSTM with skip connections from each layer to the final output. Representative LSTMs have 1024 hidden units in each direction of each layer. An 1-hot encoding of the amino acid sequence is fed as the input to the first layer. Given a sequence input, x, of length L, this sequence is 1-hot encoded into a matrix, O, of size L×21 where entry $o_{i,j}=1$ if $x_i=j$ (that is, amino acid $x_i$ has index j) and $o_{i,j}=0$ otherwise. Then, calculate $H^{(1)}=f^{(1)}(O)$, $H^{(2)}=f^{(2)}(H^{(1)})$, $H^{(3)}=f^{(3)}(H^{(2)})$, and $Z=[H^{(1)} H^{(2)} H^{(3)}]$, where $H^{(a)}$ is the hidden units of the ath layer and $f^{(a)}$ is ath BiLSTM layer. The final output of the encoder, Z, is the concatenation of the hidden units of each layer along the embedding dimension.

The masked language modeling module is now described. Preferably, a masked language modeling objective is used for training on sequences only. During training, up to 10% of the amino acids in a sequence are randomly replaces with either an auxiliary mask token or a uniformly random draw from the amino acids and train our model to predict the original amino acids at those positions. Given an input sequence, x, randomly mask this sequence to create a new sequence, x'. This sequence is fed into the encoder to give a sequence of vector representations, Z. These vectors are decoded into a distribution over amino acids at each position, p, using a linear layer. The parameters of this layer are learned jointly with the parameters of the encoder network. Calculate the masked language modeling loss as the negative log likelihood of the true amino acid at each of the masked positions, $$L_{masked} = -\frac{1}{n}\Sigma_i \log p_{i,x_i}$$

where there are n masked positions indexed by i.

The residue-residue contact prediction module is now described. Intra-residue contacts are predicted using a bilinear projection of the sequence embeddings. In particular, given a sequence, x, with embeddings, Z, calculated using the encoder network, the bilinear projection calculates $ZWZ^T+b$, where W and b are learnable parameters of dimension D×D and 1 respectively where D is the dimension of an embedding vector. These parameters are fit together with the parameters of the encoder network. This produces an L×L matrix, where L is the length of x. The i,jth entry in this matrix is then interpreted as the log-likelihood ratio between the probability that the ith and jth residues are within 8 angstroms in the 3D protein structure and the probability that they are not. The contact loss, $L_{contact}$, is then calculated as the negative log-likelihood of the true contacts given the predict contact probabilities.

The structure similarity prediction module is now described. The structure similarity prediction module follows known methods. Given two input sequences, X and X' with lengths N and M, that have been encoded into vector representations, Z and Z', calculate reduced dimension projections, A=ZB and A'=Z'B, where B is a D×K matrix that is trained together with the encoder network parameters. K is a hyperparameter and in one embodiment is set to 100. Given A and A', calculate the inter-residue semantic distances between the two sequences as the Manhattan distance between embedding at position i in the first sequence and embedding at position j in the second sequence, $d_{i,j}=\|A_i-A'_j\|_1$. Given these distances, calculate a soft alignment between the positions of sequences X and X'. The alignment weight between two positions, i and j, is defined as $c_{i,j}=\alpha_{i,j}+\beta_{i,j}-\alpha_{i,j}\beta_{i,j}$ where $$\alpha_{i,j} = \frac{k_{i,j}}{\Sigma_{l=1}^N k_{i,l}} \text{ and } \beta_{i,j} = \frac{k_{i,j}}{\Sigma_{l=1}^M k_{l,j}} \text{ and } k_{i,j} = e^{-d_{i,j}}.$$

With the inter-residue semantic distances and the alignment weights, define a global similarity between the two sequences as the negative semantic distance between the positions averaged over the alignment, $$s = -\frac{1}{c}\Sigma_{i,j}c_{i,j}d_{i,j} \text{ where } c = \Sigma_{i,j}c_{i,j}.$$

With this global similarity based on the sequence embeddings in hand, it is compared against a ground truth similarity to calculate the gradient of a loss signal and update the parameters. Because the semantic similarity should reflect structural similarity, retrieve ground truth labels, t, from the SCOP database by assigning increasing levels of similarity to proteins based on the number of levels in the SCOP hierarchy that they share. In other words, assign a ground truth label of 0 to proteins not in the same class, 1 to proteins in the same class but not the same fold, 2 to proteins in the same fold but not the same superfamily, 3 to proteins in the same superfamily but not in the same family, and finally 4 to proteins in the same family. Then, the semantic similarity is related to these levels of structural similarity through ordinal regression. In particular, calculate the probability that two sequences are similar at a level t or higher as $p(y\geq t)=\theta_t s+b_t$ where $\theta_t$ and $b_t$ are additional learnable parameters for t≥1. The constraint that $\theta_t \geq 0$ is imposed in order to ensure that increasing similarity between the embeddings corresponds to increasing numbers of shared levels in the SCOP hierarchy. Given these distributions, calculate the probability that two proteins are similar at exactly level t as $p(y=t)=p(y\geq t)(1-p(y\geq t+1))$, i.e., the probability that two sequences are similar at exactly level t is equal to the probability they are similar at least level t times the probability they are not similar at a level above t. Then, define a structural similarity prediction loss to be the negative log-likelihood of the observed similarity labels under this model, $L_{similarity}=-\log p(y=t)$.

Given the above, define a combined multi-task loss as a weighted sum of the language modeling, contact prediction, and similarity prediction losses, namely: $L_{MT}=\lambda_{masked}L_{masked}+\lambda_{contact}L_{contact}+\lambda_{similarity}L_{similarity}$.

Protein Sequence Analysis

Figure 4C:
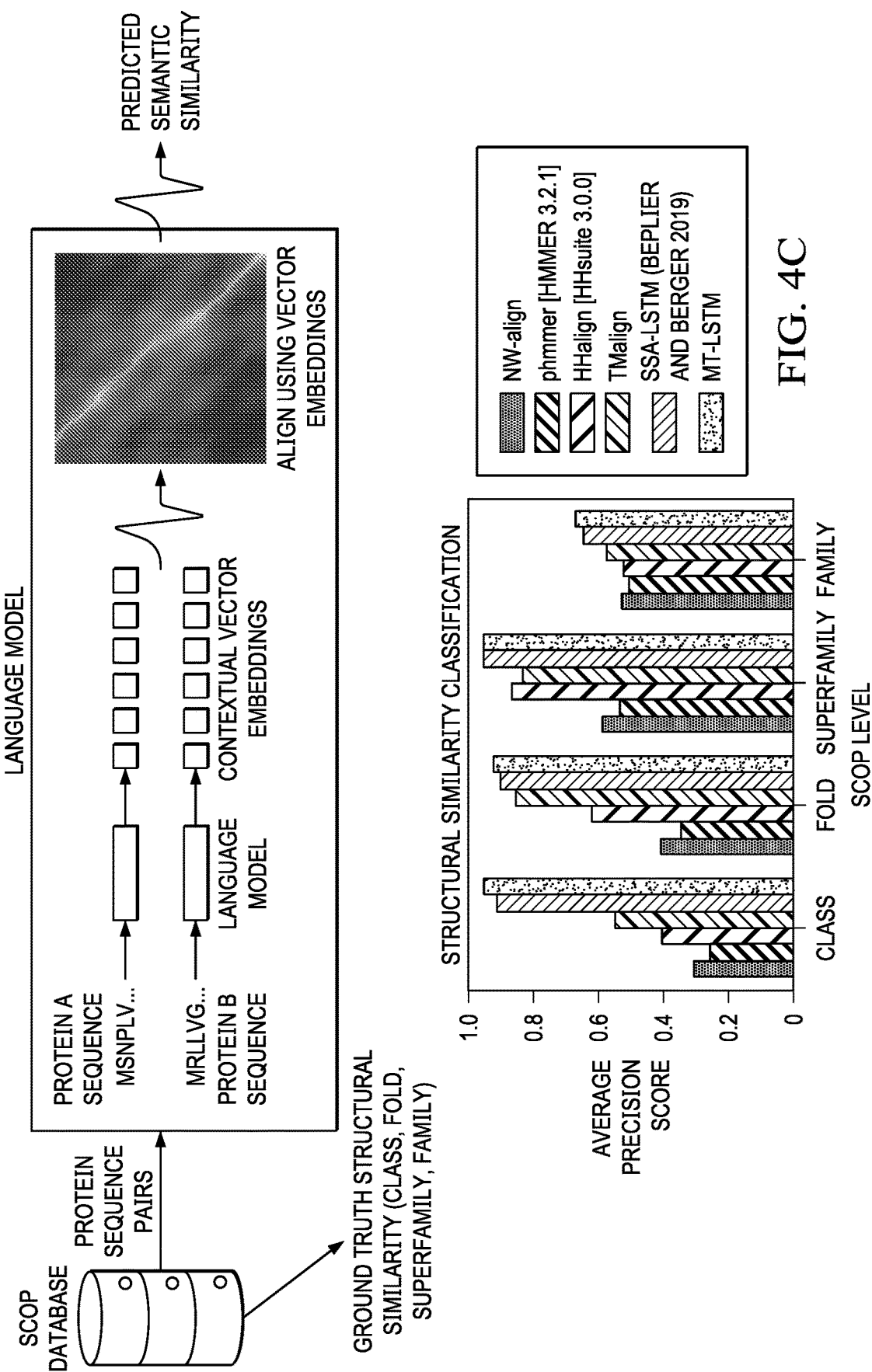

FIGS. 4A, 4B and 4C depict how the trained language model is then used for protein sequence analysis according to this disclosure. As depicted at FIG. 4A, and given the trained language model 400 (the neural network), the protein sequences 402 are embedded by processing them with the neural network and taking the hidden layer representations for each position of the sequence. This products an L×D matrix 404 containing a D-dimensional vector embedding for each position of a length L sequence. The matrix 404 is then reduced (e.g., by a pooling operation, such as averaging) to a D-dimensional vector 406 summarizing the entire sequence. These representations allow the system to directly visualize large protein datasets with manifold embedding techniques. As depicted at FIG. 4B, manifold embedding of SCOP protein sequences reveals that the language model learns protein sequence representations that capture structural semantics of proteins. In particular, thousands of protein sequences from the SCOP database are embedded, and the t-SNE plots of the embedded proteins colored by SCOP structural class are depicted. A masked language (unsupervised) model (DLM-LSTM) learns embeddings that separate protein sequences by structural class (as shown in plot 408, whereas the multi-task language model (MT-LSTM) with structural supervision learns an even better organized embedding space (as shown in plot 410). In contrast, manifold embedding of sequences directly (edit distance) produces an unintelligible plot 412 and does not resolve structural groupings of proteins. As depicted at FIG. 4C, and in order to quantitatively evaluate the quality of the learned semantic embeddings, a correspondence between semantic similarity predicted by the language model representations and ground truth structural similarities between proteins in the SCOP database is calculated. In particular, and given two proteins, one can calculate the semantic similarity between them by embedding these proteins using the MT-LSTM, align the proteins using the embeddings, and calculate an alignment score. The average-precision score for retrieving pairs of proteins similar at different structural levels in the SCOP hierarchy are computed based on this predicted semantic similarity.

Thus, and as depicted in FIGS. 4A, 4B and 4C, the trained language model is useful for protein sequence analysis. As described, and given the trained MT-LSTM, new protein sequences are applied to embed them into the learned semantic representation space (a vector space). Sequences are fed through the model and the hidden layer vectors are combined to form vector embeddings of each position of the sequences; preferably, no multiple sequence alignment is used. Given a sequence of length L, this yields L D-dimensional vectors, where D is the dimension of the vector embeddings. This allows the system to map the semantic space of each residue within a sequence, as well as to map the semantic space of whole sequences by summarizing them into fixed size vector embeddings via a reduction operation. Practically, this is useful for coarse sequence comparisons including clustering and manifold embedding for visualization of large protein datasets, revealing evolutionary, structural, and functional relationships between sequences in the dataset (FIG. 4B). As depicted, proteins in the SCOP dataset are visualized, colored by structural class, after embedding with MT-LSTM (FIG. 4B, 410). For comparison, the results of embedding using a bidirectional LSTM trained only with the masked language modeling objective (DLM-LSTM) (FIG. 4B, 408), which is not enriched with the structure-based priors. A skilled person will observe that even though the DLM-LSTM model was trained using only sequence information, protein sequences still organize roughly by structure in embedding space. This organization is improved by including the structure supervision in the language model training, as has been described.

The semantic organization of the learned embedding space enables efficient searching of protein sequence databases for semantically related proteins and, in particular, by comparing proteins based on their vector embeddings. Because the approach herein embeds sequences into a semantic representation space, the system finds structurally related proteins even though their sequences are not directly closely related. To demonstrate this, pairs of proteins in the SCOP database that are not seen by the multi-task model during training are taken, and the similarity between these pairs of sequences are calculated using direct sequence homology-based methods (Needleman-Wunsch alignment, HMM-sequence alignment, and HMM-HMM alignment), a popular structure-based method (TMalign), and an alignment between the sequences in the learned embedding space. These methods were then evaluated based on their ability to correctly find pairs of proteins that are similar at the class, fold, superfamily, and family levels, based on their SCOP classification. The result of this analysis is depicted at plot 414. In particular, the learned semantic embeddings of this disclosure dramatically outperform the sequence comparison methods and even outperform structure comparison with TMalign, which predicts structural similarity from structures directly. The multi-task learning approach also outperforms a two-step learning approach presented previously (SSA-LSTM).

Transfer Learning

Figure 5A:
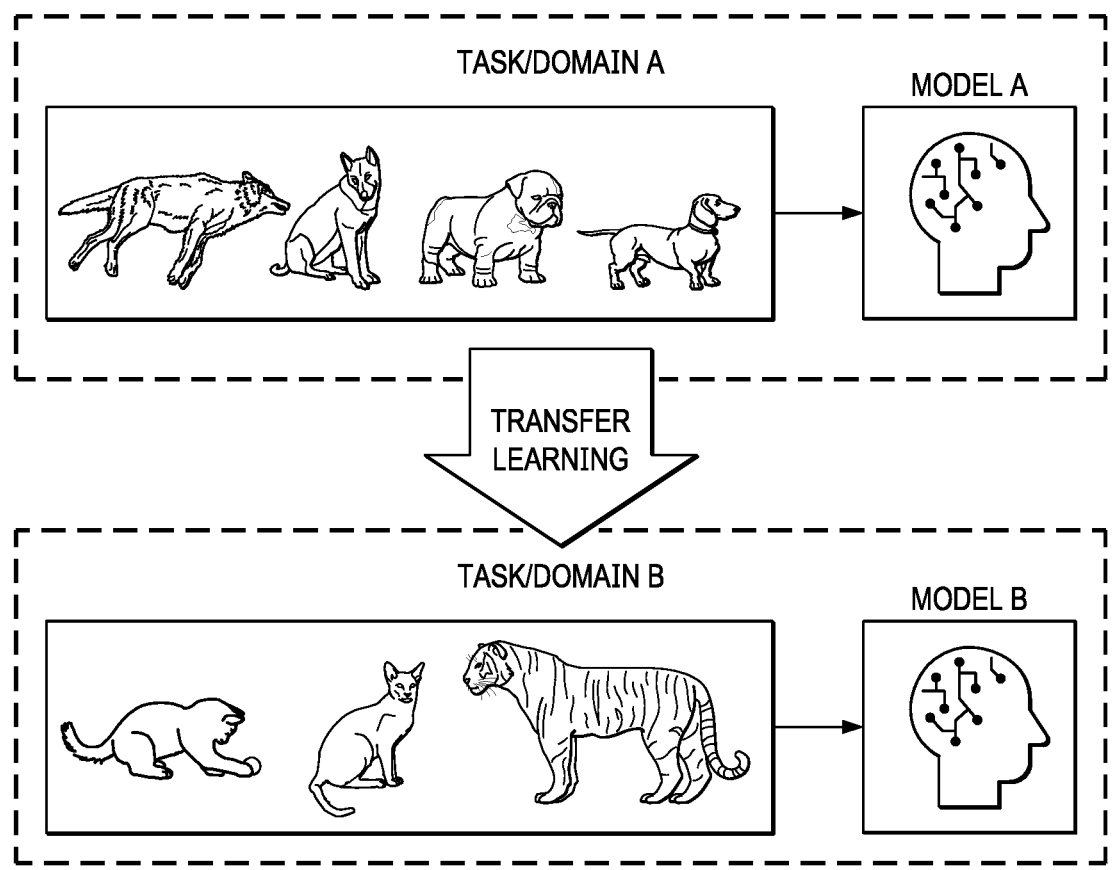

As depicted in FIG. 5A, transfer learning is the problem of applying knowledge gained from learning to solve some task, A, to another related task, B, e.g., applying knowledge from recognizing dogs to recognizing cats. Usually, transfer learning is used to improve performance on tasks with little available data by transferring knowledge from other tasks with large amounts of available data. In the case of proteins, it is desired to apply knowledge from evolutionary sequence modeling and structure modeling to protein function prediction tasks. In one example, and as shown at FIG. 5B, transfer learning is used to improve transmembrane prediction. This is a sequence labeling task in which the amino acid sequence of a protein is provided and it is desired to decode, for each position of the protein, whether that position is in a transmembrane (i.e., membrane spanning) region of the protein or not. This problem is complicated by the presence of signal peptides, which are often confused as transmembrane regions.

In this example, a transmembrane prediction model comprises two components. First, the protein sequence is embedded using the above-described pre-trained language model (MT-LSTM) 502 by taking the hidden layers of the language model at each position. Then, these representations are fed into a small single layer bidirectional LSTM (BiLSTM) 504, and the output thereof is fed into a conditional random field (CRF) 506 to predict the transmembrane label at each position. The model is evaluated, e.g., by 10-fold cross validation on proteins split into four categories: transmembrane only (TM), signal peptide and transmembrane (TM+SP), globular only (Globular), and globular with signal peptide (Globular+SP). A protein is considered correctly predicted if (i) the presence or absence of signal peptide is correctly predicted. and (ii) the number of locations of transmembrane regions is correctly predicted. The table 508 reports the fraction of correctly predicted proteins in each category for the model (BiLSTM+CRF) and for widely used transmembrane prediction methods. As can be seen, a BiLSTM+CRF model trained using 1-hot embeddings of the protein sequence instead of the language model representations performs poorly, highlighting the importance of transfer learning for this task.

Figure 5C:
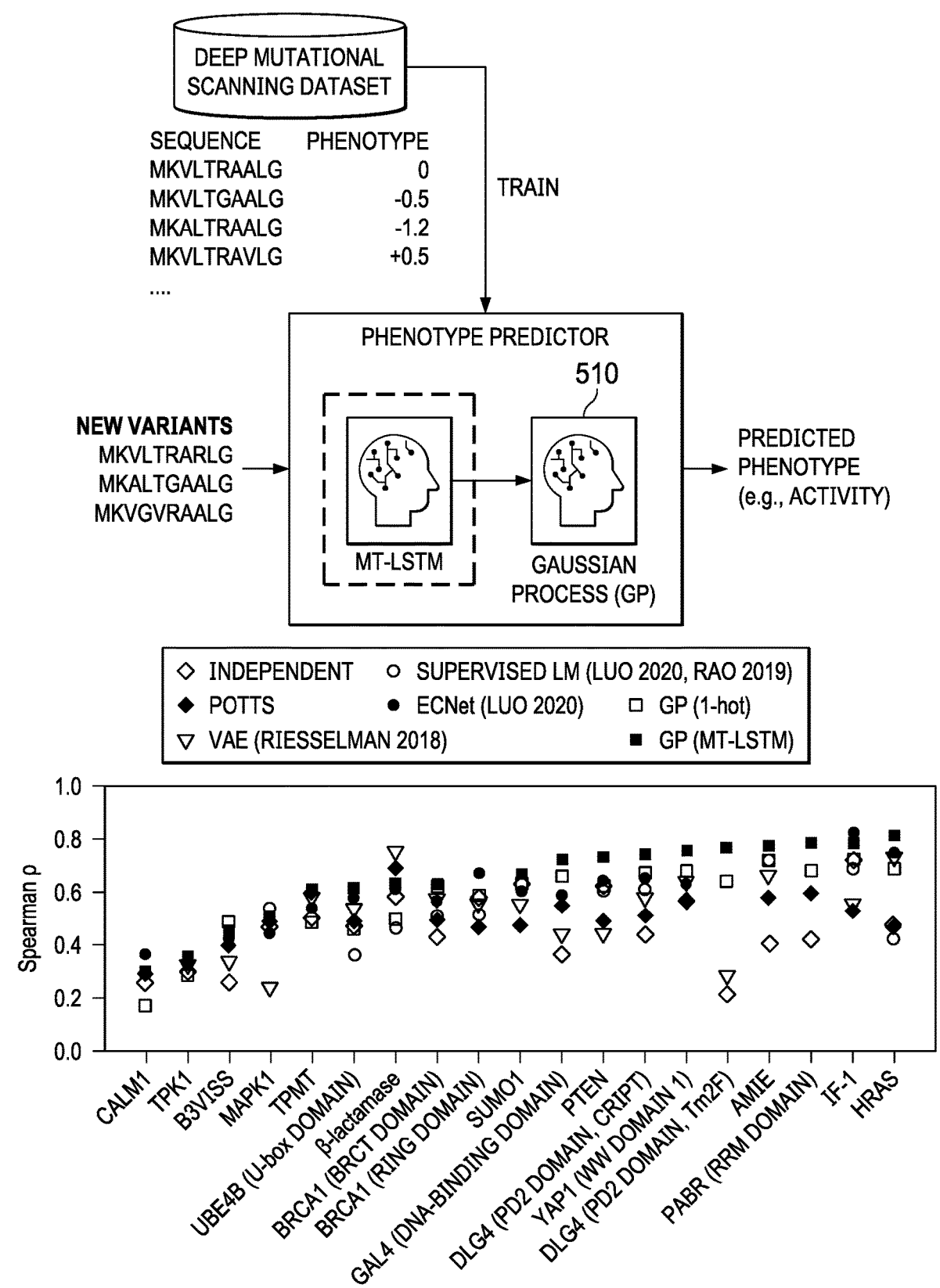

In another example, and as shown in FIG. 5C, transfer learning is used to improve sequence-to-phenotype prediction. Deep mutational scanning measures function for thousands of protein sequence variants. In this example, nineteen (19) mutational scanning datasets spanning a variety of proteins and phenotypes are considered. For each dataset, the sequence-to-phenotype mapping is learned by fitting a Gaussian process regression model on top of representations given by the above-described pre-trained language model. Then, a comparison was made of three unsupervised approaches (+), prior works in supervised learning (o), and the Gaussian process regression approaches with (GP (MT-LSTM)) and without (GP (1-hot)) transfer learning by 5-fold cross validation. Spearman rank correlation coefficients between predicted and ground truth functional measurements are plotted at 510. As can be seen, the GP with transfer learning outperforms all other methods, having an average correlation of 0.65 across datasets. The benefits of transfer learning are highlighted by the improvement over the 1-hot representations which only reach 0.57 average correlation across datasets. Transfer learning improves performance on 18 out of 19 datasets.

Summarizing, the approach enables the learning of vector representations of protein sequences using information from structure. Transferring structure (and sequence) knowledge through these representations greatly improves downstream prediction tasks, such as detecting structurally-related proteins, transmembrane prediction, phosphorylation site prediction, predicting general enzyme function, detecting Bt toxins, drug-target interaction prediction, and the like.

Figure 6:
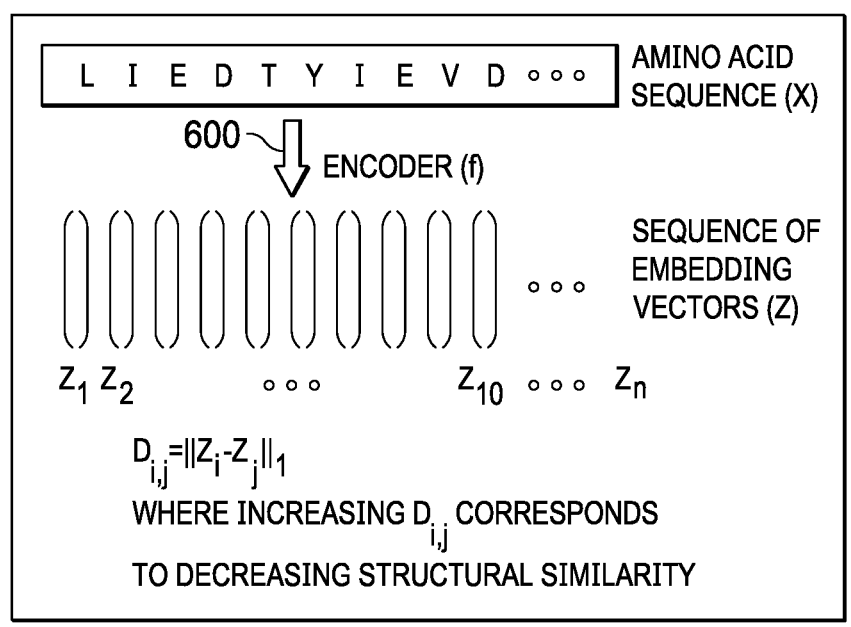
FIG. 6 depicts a simplified representation of how sequences of amino acids are embedded into sequences of vectors encoding structural information according to this disclosure.

As has been described, the approach herein advantageously embeds sequences of amino acids into sequences of vectors encoding structural information. FIG. 6 depicts the high level process. To this end, an encoder function $f$ 600 that transforms observed protein sequences X into sequences Z of vectors is learned. The function captures structure information in these vector embeddings. In one embodiment, metric embedding, namely, distances in embedding (vector) space, then encode structural similarity. Metric embeddings allow exact search in O(log N) time. In the alternative, approximate search can be carried out in vector space using locality sensitive hashing, and in constant time. The specialized models as described herein detect in constant time and do not require database search.

Figure 8:
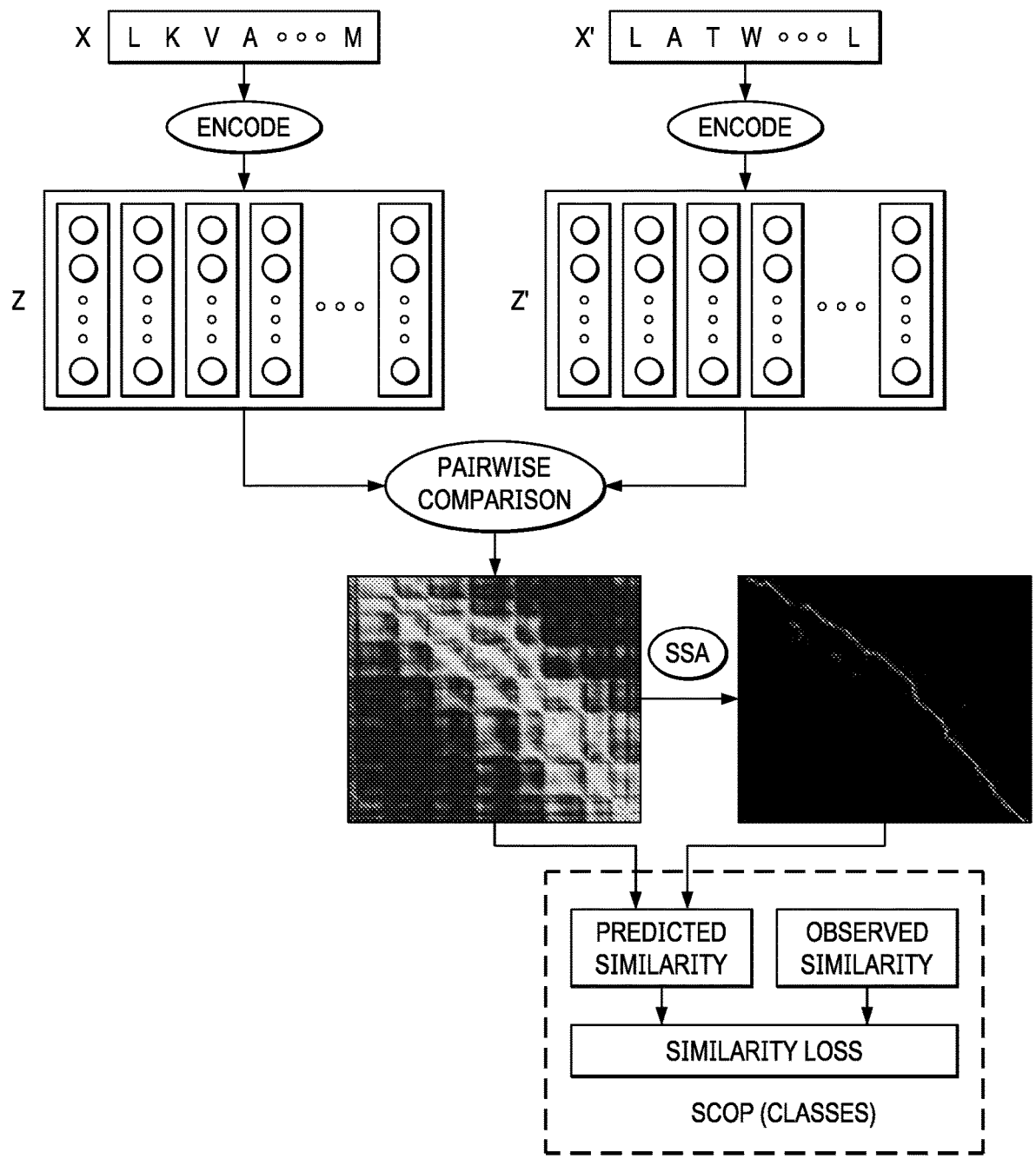
FIG. 8 depicts a learning sequence embedding model with weak supervision from global similarity.
Figure 9:
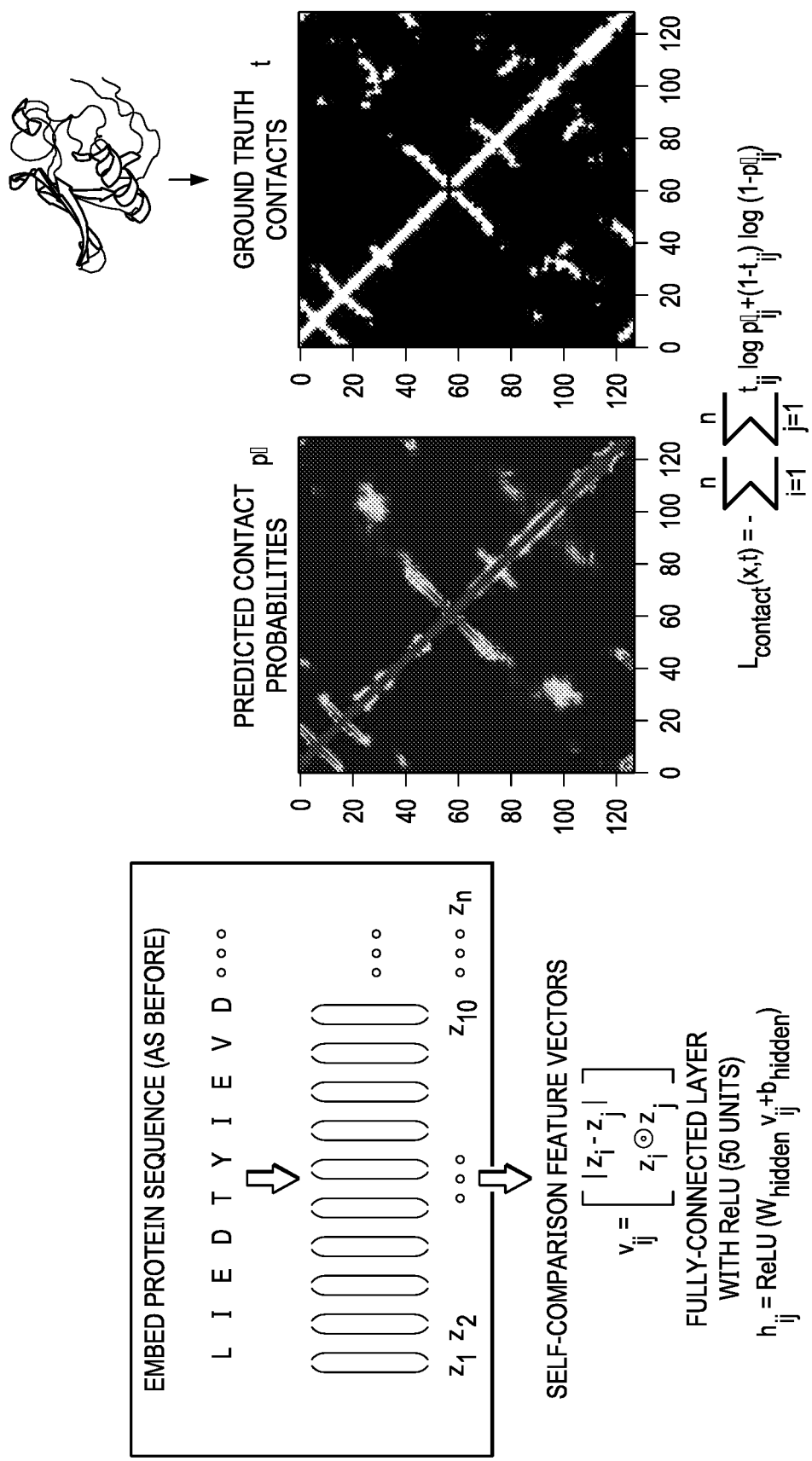
FIG. 9 depicts improving the embeddings by predicting residue-residue contacts.
Figure 10:
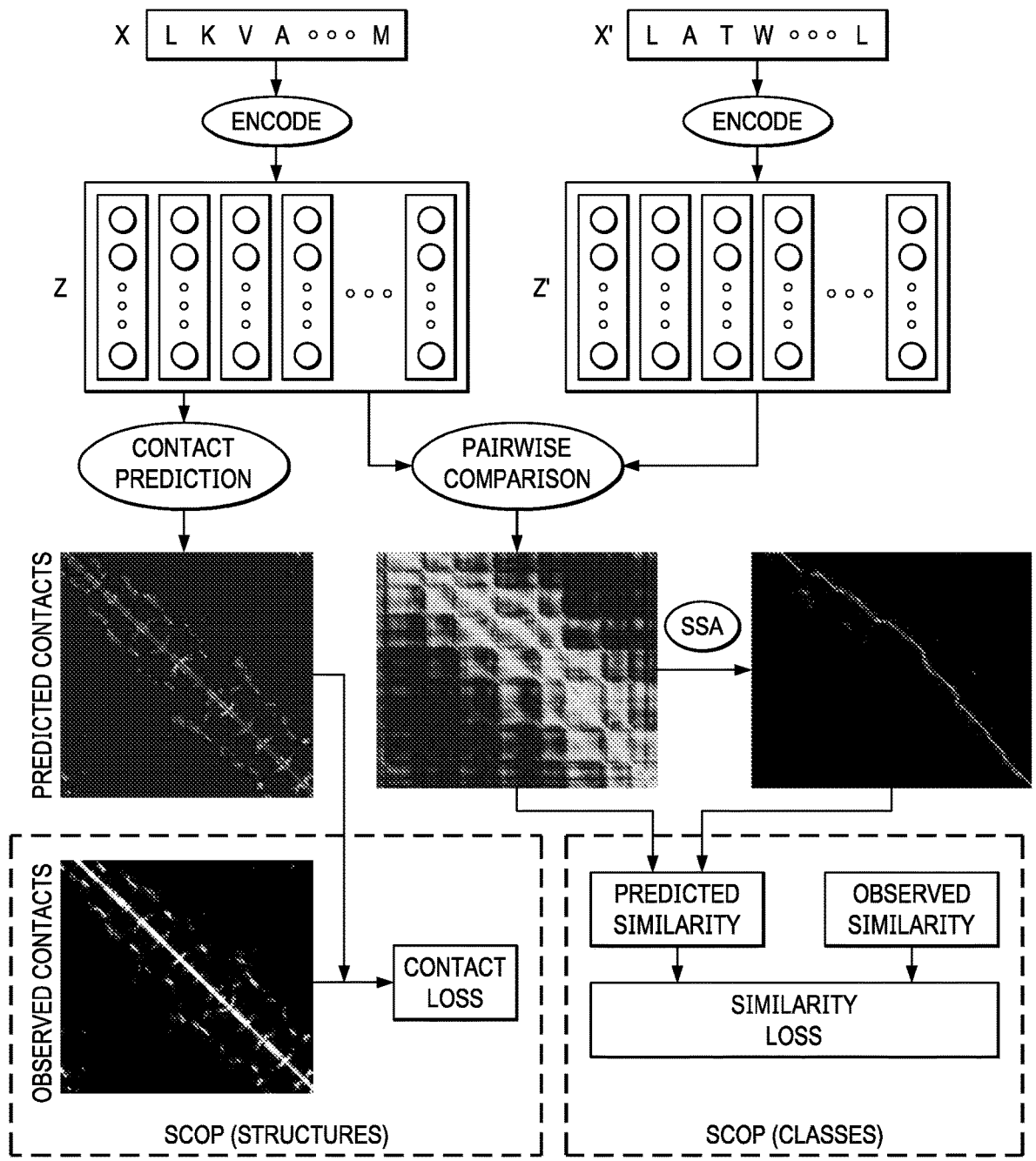
FIG. 10 depicts learning from global structural similarity between proteins and residue-residue contacts within proteins.

For metric embedding, FIG. 7 depicts one technique for modeling global similarity using and, in particular, using soft symmetric alignment (SSA). FIG. 8 depicts a learning sequence embedding model with weak supervision from global similarity determined in this manner. FIG. 9 depicts improving the embeddings by predicting residue-residue contacts. FIG. 10 depicts learning from global structural similarity between proteins and residue-residue contacts within proteins.

Enabling Technologies

Aspects of this disclosure may be practiced, typically in software, on one or more machines or computing devices. More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines. A computing device connects to the publicly-routable Internet, an intranet, a private network, or any combination thereof, depending on the desired implementation environment.

One implementation may be a machine learning-based computing platform. One or more functions of the computing platform may be implemented in a cloud-based architecture. The platform may comprise co-located hardware and software resources, or resources that are physically, logically, virtually and/or geographically distinct. Communication networks used to communicate to and from the platform services may be packet-based, non-packet based, and secure or non-secure, or some combination thereof.

Each above-described process or process step/operation preferably is implemented in computer software as a set of program instructions executable in one or more processors, as a special-purpose machine.

Representative machines on which the subject matter herein is provided may be hardware processor-based computers running a Linux or Linux-variant operating system and one or more applications to carry out the described functionality. One or more of the processes described above are implemented as computer programs, namely, as a set of computer instructions, for performing the functionality described.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system such as Linux. A machine implementing the techniques herein comprises a hardware processor, and non-transitory computer memory holding computer program instructions that are executed by the processor to perform the above-described methods.

There is no limitation on the type of computing entity that may implement a function or operation as described herein. While given components of the system have been described separately, one of ordinary skill will appreciate that some of the functions may be combined or shared in given instructions, program sequences, code portions, and the like. Any application or functionality described herein may be implemented as native code, by providing hooks into another application, by facilitating use of the mechanism as a plug-in, by linking to the mechanism, and the like.

The functionality may be co-located or various parts/components may be separately and run as distinct functions, perhaps in one or more locations (over a distributed network).

Computing entities herein may be independent from one another, or associated with one another. Multiple computing entities may be associated with a single enterprise entity, but are separate and distinct from one another.

As a variant technique, it may be desired to use the learned embedding model to facilitate generation of a simple classifier that is trained to distinguish one set of proteins (being of interest) from another set of proteins (not being of interest). In such case, the classifier may then be used to score proteins in the database (e.g., as relevant or not relevant) in order to return the most relevant search results. To perform a search, all (or some given number) of the query sequences are first embedded with the embedding model into the embedding (vector) space and then fitted to a classifier to classify into the "of interest" or "not of interest" categories based on their vector embeddings. In other words, the protein sequences are pre-processed into one or more parameters of the classifier. Then, the classifier is used to search the database, e.g., by scoring every protein in the database as being either not relevant or relevant according to the classifier as trained.

What is claimed here follows below.

The invention claimed is:

1. A method for efficient search of protein sequence databases for proteins that have sequence, structural, and/or functional homology, comprising:
training a model to learn a function that maps protein sequences, represented as sequences of amino acids, to sequences of vector representations in a vector space, the model having a set of parameters that are estimated to minimize a loss function over training data, wherein the loss function comprises a denoising/masked modeling term, a structural similarity metric embedding term, and a residue-residue contact prediction term;
providing a database of protein sequences and their associated sequences of vector representations as determined by the model;
responsive to receipt of a query for a protein or protein sequence, using the model to convert the query into a sequence of one or more vector representations; and
performing a search in vector space against the database using the one or more vector representations to obtain a result, the result being obtained in sub-linear time.

2. The method as described in claim 1 wherein the loss function is a weighted sum of the loss function terms.

3. The method as described in claim 2 wherein the model and the loss function terms are derived concurrently as the model is trained.

4. The method as described in claim 1 wherein the search is an exact search of the database using metric data structures to identify one or more nearest proteins, as represented by the one or more vector representations, in the vector space.

5. The method as described in claim 4 further including preprocessing the database to organize the vector representations of the proteins into a search tree.

6. The method as described in claim 5 wherein the search tree is one of: a ball tree, and a K-D tree.

7. The method as described in claim 1 wherein the search returns the protein or protein sequence as represented by embeddings in the vector space.

8. The method as described in claim 1 wherein the model is a neural network.

9. The method as described in claim 8 wherein the neural network is one of: a recurrent neural network, a convolutional neural network, and a transformer.

10. The method as described in claim 8 wherein the model is a bidirectional Long Short Term Memory (LSTM) trained to solve a set of tasks concurrently.

11. The method as described in claim 10 wherein the set of tasks comprise a self-supervised masked language modeling task on natural protein sequences, a supervised residue-residue contact prediction task, and a supervised structural similarity prediction task.

12. The method as described in claim 1 wherein the set of parameters are determined using stochastic gradient descent.

13. A method for efficient search of protein sequence databases for proteins that have sequence, structural, and/or functional homology, comprising:
training a model to learn a function that maps protein sequences, represented as sequences of amino acids, to sequences of vector representations in a vector space, the model having a set of parameters that are estimated to minimize a loss function over training data;
providing a database of protein sequences and their associated sequences of vector representations as determined by the model;
responsive to receipt of a query for a protein or protein sequence, using the model to convert the query into a sequence of one or more vector representations; and
performing a search in vector space against the database using the one or more vector representations to obtain a result, the result being obtained in sub-linear time, wherein the search is performed using locality sensing hashing;
wherein the locality sensitive hashing comprises:
placing vector representations into a set of indexed buckets based on their locations in the vector space;
applying a hash function to the sequence of one or more vector representations of the query to identify one of the set of indexed buckets; and
returning, as the result, one or more proteins found in the identified indexed bucket.

14. An apparatus, comprising:
one or more processors;
computer memory holding computer program code executed by the one or more processors for efficient search of protein sequences for proteins that have sequence, structural, and/or functional homology, wherein the computer program code is configured to:
train a model to learn a function that maps protein sequences, represented as sequences of amino acids, to sequences of vector representations in a vector space,
the model having a set of parameters that are estimated to minimize a loss function over training data, wherein the loss function comprises a denoising/masked modeling term, a structural similarity metric embedding term, and a residue-residue contact prediction term;
save protein sequences and their associated sequences of vector representations as determined by the model in a data store;
responsive to receipt of a query for a protein or protein sequence, use the model to convert the query into a sequence of one or more vector representations; and
perform a search in vector space against the data store using the one or more vector representations to obtain a result, the result being obtained in sub-linear time.

15. The apparatus as described in claim 14 wherein the model is a bidirectional Long Short Term Memory (LSTM) trained to solve a set of tasks concurrently, the set of tasks comprising a self-supervised masked language modeling task on a first corpus of natural protein sequences, and at least one other supervised structural similarity task on a second corpus of protein sequences.

16. A computer program product comprising a non-transitory computer-readable medium for use in a data processing system for efficient search of protein sequences for proteins that have sequence, structural, and/or functional homology, the computer program product hold computer program instructions that, when executed by the data processing system:
train a model to learn a function that maps protein sequences, represented as sequences of amino acids, to sequences of vector representations in a vector space, the model having a set of parameters that are estimated to minimize a loss function over training data, wherein the loss function comprises a denoising/masked modeling term, a structural similarity metric embedding term, and a residue-residue contact prediction term;

save protein sequences and their associated sequences of vector representations as determined by the model in a data store;

responsive to receipt of a query for a protein or protein sequence, use the model to convert the query into a sequence of one or more vector representations; and perform a search in vector space against the data store using the one or more vector representations to obtain a result, the result being obtained in sub-linear time.

17. The computer program product as described in claim 16 wherein the model is bidirectional Long Short Term Memory (LSTM) trained to solve a set of tasks concurrently, the set of tasks comprising a self-supervised masked language modeling task on a first corpus of natural protein sequences, and at least one other supervised structural similarity task on second corpus of protein sequences.

* * * * *